US009855387B2

(12) United States Patent
Small et al.

(10) Patent No.: US 9,855,387 B2
(45) Date of Patent: Jan. 2, 2018

(54) MEDICAL FLUID INJECTOR SYSTEM

(75) Inventors: James R. Small, Beavercreek, OH (US); Jeffrey A. Perkins, Mainville, OH (US); Frank M. Fago, Mason, OH (US); Mark Jon Glenn, Phoenix, AZ (US)

(73) Assignee: LIEBEL-FLARSHEIM COMPANY LLC, Cincinnati, OH (US)

( * ) Notice: Subject to any disclaimer, the term of this patent is extended or adjusted under 35 U.S.C. 154(b) by 253 days.

(21) Appl. No.: 13/988,800

(22) PCT Filed: Nov. 21, 2011

(86) PCT No.: PCT/US2011/061605
§ 371 (c)(1),
(2), (4) Date: May 22, 2013

(87) PCT Pub. No.: WO2012/071307
PCT Pub. Date: May 31, 2012

(65) Prior Publication Data
US 2013/0245439 A1    Sep. 19, 2013

Related U.S. Application Data

(60) Provisional application No. 61/417,091, filed on Nov. 24, 2010.

(51) Int. Cl.
*A61M 5/30* (2006.01)
*A61M 5/20* (2006.01)
(Continued)

(52) U.S. Cl.
CPC ........ *A61M 5/2066* (2013.01); *A61M 5/1407* (2013.01); *A61M 5/14546* (2013.01);
(Continued)

(58) Field of Classification Search
CPC .... A61M 5/142; A61M 5/145; A61M 5/1452; A61M 2005/14208
(Continued)

(56) References Cited

U.S. PATENT DOCUMENTS 5,121,603 A * 6/1992 Widemann ............... 60/447
6,796,955 B2 * 9/2004 O'Mahony et al. ......... 604/6.11
(Continued)

FOREIGN PATENT DOCUMENTS

JP    2003-290343 A1    10/2003
WO   2003097128 A1    11/2003
(Continued)

*Primary Examiner* — Kevin C Sirmons
*Assistant Examiner* — Leah Swanson
(74) *Attorney, Agent, or Firm* — Marsh Fischmann & Breyfogle LLP

(57) ABSTRACT

A medical fluid injector system (450) is disclosed that may utilize one or more of flow rate determination logic (130), injection volume determination logic (132), display control logic (134), drive ram motion control logic (136), and pressure monitoring logic (138). The flow rate determination logic (130), injection volume determination logic (132), and display control logic (134) each may utilize a concentration input (172, 192, 202) to calculate flow rates, injection volumes, and generate multi-color graphics, respectively, for a simultaneous injection configuration. The drive ram motion control logic (136) may utilize both a target pressure and a monitored pressure to derive a velocity for advancing a drive ram. The pressure monitoring logic (138) may provide a monitored pressure value for the drive ram control logic (136), where this monitored pressure value may be derived from the input power being used to advance a drive ram and the drive ram velocity.

22 Claims, 17 Drawing Sheets

(51) Int. Cl.
 *A61M 5/14* (2006.01)
 *A61M 5/145* (2006.01)
 *A61M 5/168* (2006.01)
 *A61B 6/00* (2006.01)

(52) U.S. Cl.
 CPC ......... *A61M 5/16827* (2013.01); *A61B 6/548* (2013.01); *A61M 2205/502* (2013.01)

(58) Field of Classification Search
 USPC .................................. 600/432; 604/67, 131
 See application file for complete search history.

(56) References Cited

U.S. PATENT DOCUMENTS

| | | |
|---|---|---|
| 6,929,751 B2* | 8/2005 | Bowman et al. ............ 210/741 |
| 8,444,592 B2 | 5/2013 | Williams |
| 2005/0070874 A1 | 3/2005 | Matsuda |
| 2007/0154319 A1* | 7/2007 | Stiles et al. .................... 417/42 |
| 2008/0183060 A1* | 7/2008 | Steil et al. .................... 600/365 |
| 2010/0228222 A1* | 9/2010 | Williams ............ A61M 1/0058 604/500 |

FOREIGN PATENT DOCUMENTS

| | | |
|---|---|---|
| WO | 2005102416 | 11/2005 |
| WO | 2007050771 A1 | 3/2007 |
| WO | 2009067212 A1 | 5/2009 |
| WO | 2010062931 | 6/2010 |
| WO | 2010027636 A1 | 11/2010 |

\* cited by examiner

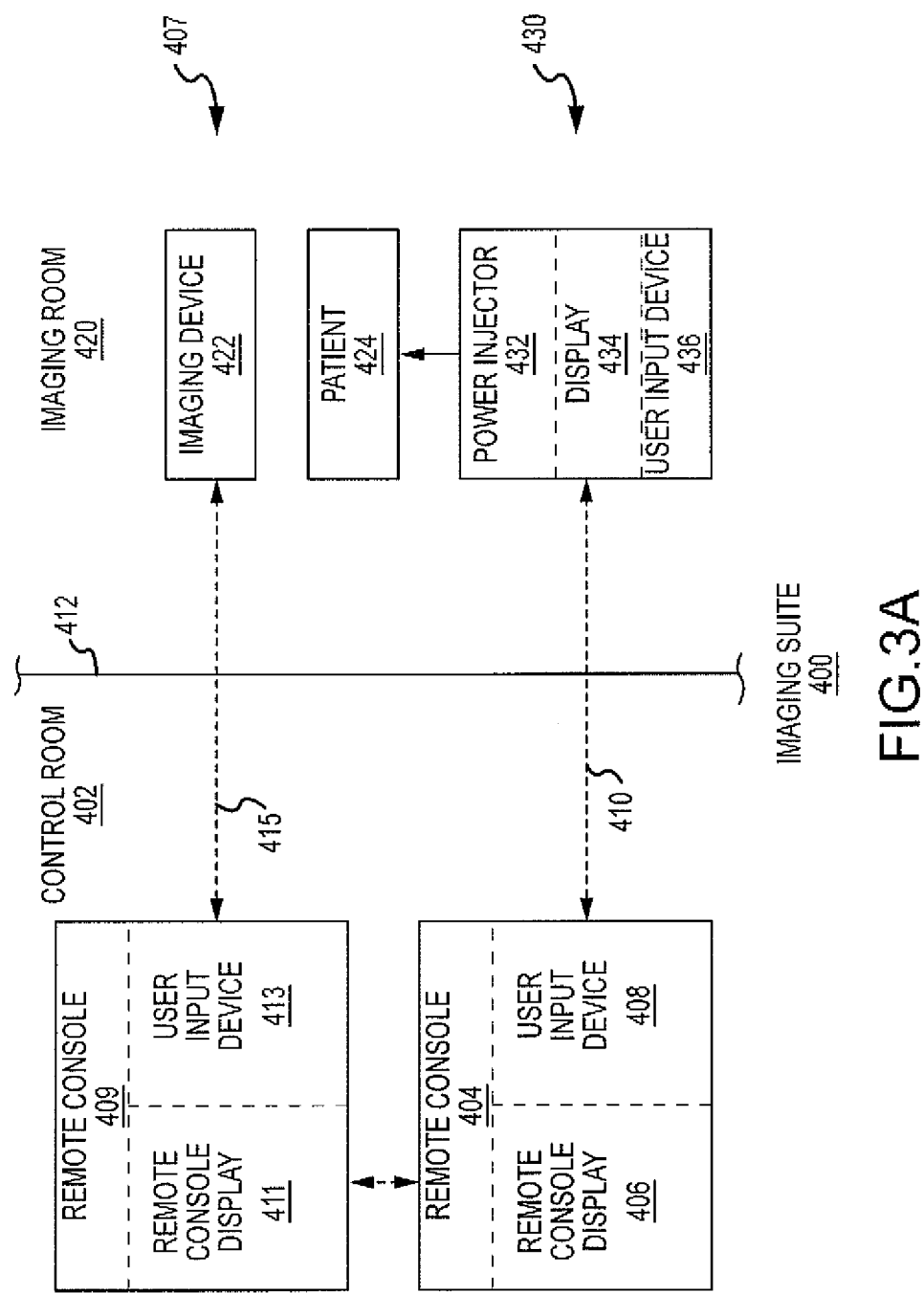

MEDICAL FLUID INJECTOR SYSTEM

RELATED APPLICATIONS

This patent application is a U.S. National Stage of PCT/US2011/061605, filed 21 Nov. 2011, which claims priority to and is a non-provisional application of U.S. Provisional Patent Application Ser. No. 61/417,091 filed on 24 Nov. 2010 entitled "MEDICAL FLUID INJECTOR SYSTEM". Priority is claimed to each patent application set forth in this Cross-Reference to Related Applications section.

FIELD OF THE INVENTION

The present invention generally relates to the field of systems that are used to inject one or more medical fluids into a target, such as a patient.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

SUMMARY

The various aspects of the present invention may be utilized in relation to the execution of an injection protocol. An injection protocol may include one or more phases that may be programmed in any appropriate manner. Each phase of an injection protocol may include injection parameters such as a total amount of fluid to be injected and an injection flow rate, as well as possibly one or more injection delays (sometimes referred to as "holds" and/or "pauses") and each of which can be of finite or infinite duration. A phase of an injection protocol may be directed to injecting a single liquid at a single injection site. A phase of an injection protocol may be directed to simultaneously injecting multiple fluids (e.g., contrast media and saline) at a single injection site.

A first aspect of the present invention is directed to deriving at least one drive ram velocity increase from a target pressure in the context of a medical fluid injector system. The first aspect may be in the form of a medical fluid injector system that includes both a syringe plunger driver and drive ram motion control logic, where the syringe plunger driver includes both a drive source (e.g., a motor of any appropriate type) and a drive ram (e.g., an axially movable structure), and where the drive ram motion control logic is configured to derive a drive ram velocity increase from a target pressure for the associated drive ram. The first aspect may also be in the form of a method of injecting at least one fluid using a medical fluid injector system, where data for a target pressure for an injection protocol is entered (e.g., input to the medical fluid injector system), and where a velocity increase for a drive ram of the medical fluid injector system is derived from this target pressure.

A number of feature refinements and additional features are applicable to the first aspect of the present invention. These feature refinements and additional features may be used individually or in any combination. As such, each of the following features that will be discussed may be, but are not required to be, used with any other feature or combination of features of the first aspect. The following discussion is applicable to the first aspect, up to the start of the discussion of a second aspect of the present invention.

The first aspect may be characterized as being directed to using a target pressure to control how the velocity of at least one drive ram of the medical fluid injector system is increased during at least part of at least one phase of an injection protocol. The first aspect could be implemented to control how the velocity of one or more drive rams of a medical fluid injector system should be increased during any relevant portion of an injection protocol and based upon the target pressure. The first aspect may be used in the execution of any appropriate number of phases of a given injection protocol, at any time or times during a given phase, and regardless of the number of drive rams being advanced during a given phase (e.g., the target pressure may be used to control a velocity increase of a single ram during a given phase; the target pressure may be used to control a velocity increase of multiple drive rams in a given phase—what may be characterized as a simultaneous injection phase). In one embodiment, a single target pressure is associated with the entire injection protocol, regardless of the number of phases (e.g., the same target pressure may be used in relation to each phase of an injection protocol).

The target pressure may be set in response to user input, where this user input is in the form of a value input to the medical fluid injector system in any appropriate manner (e.g., via a data input device of any appropriate type) and at any appropriate location (e.g., from a remote console of the medical fluid injector system; from a powerhead of a power injector of the medical fluid injector system; from a console that is common to both a power injector of the medical fluid injector system, and a scanner or other medical imaging device). A pressure-related prompt (e.g., a prompt for a peak pressure; a prompt for a target pressure) may be presented on one or more displays of the medical fluid injector system at one or more locations. One or more data input devices may be made available to enter a value for a pressure in conjunction with the noted pressure-related prompt. The value for the target pressure could be set to the same value as the value that was input for a peak pressure, or the target pressure could be defined from the value that was input for a peak pressure (e.g., in accordance with an algorithm, such as target pressure=peak pressure minus 25 psi). Any value that is entered for a peak pressure may be characterized as data that may be used to set the target pressure.

Although the velocity of one or more drive rams of the medical fluid injector system could be continually increased throughout at least one phase of an injection protocol and based upon target pressure in the case of the first aspect, such need not be the case. The target pressure may be used to control the manner in which the velocity of a given drive ram is increased from the time that a particular phase is initiated until some later point in time (e.g., until the target pressure is actually reached; until a target flow rate for the associated phase is reached; until the conclusion of the associated phase). Any appropriate initial velocity may be utilized for purposes of an original derivation of drive ram velocity for a given phase, including a zero velocity. After the velocity of a given drive ram of the medical fluid injector system has been increased for some period of time, the velocity of this drive ram could be maintained at a certain value and/or could actually be reduced. However, any subsequent velocity increase(s) for this drive ram may still be derived from the original target pressure and in accordance with the first aspect.

The target pressure may be characterized as being an independent variable, while a derived velocity for a given drive ram of the medical fluid injector system may be characterized as being a dependent variable. A drive ram velocity derivation may be characterized as depending upon and/or being influenced by at least the target pressure. In one embodiment, the target pressure (e.g., a target pressure value) may be an input to a drive ram motion control algorithm, and the output of this drive ram motion control algorithm may be a drive ram velocity (e.g., a drive ram velocity value), If the output of this drive ram motion control algorithm is of a larger magnitude than an immediately prior-in-time execution of this same drive ram motion control algorithm, this may be characterized as a drive ram velocity increase for purposes of the first aspect. In any case, such a drive ram control algorithm could be executed on any appropriate basis, such as periodically (e.g., every 40 milliseconds, or some other appropriate time period).

At least one drive ram velocity increase derived from a target pressure may be utilized in relation to the first aspect. Multiple drive ram velocity increases may be derived in relation to the first aspect and may be undertaken (and of course implemented, i.e., used to control the velocity of the associated drive ram) on any appropriate basis. Any appropriate timing may be utilized in the case of multiple drive ram velocity derivations, Consider the case where the first aspect incrementally increases a drive ram velocity in view of the target pressure and until any occurrence of a first condition. This first condition may be the medical fluid injector system reaching the target pressure, reaching a target flow rate for an associated phase, reaching the end of an associated phase, or any combination thereof. In one embodiment, the target pressure (e.g., for the entire injection protocol), a target flow rate (e.g., for an associated phase), or both may be based upon a corresponding input to the medical fluid injector system by a user in any appropriate manner (e.g., through a data input device of any appropriate type). The derived incremental increase in drive ram velocity may be initiated at the start of a given phase of an injection protocol and may continue on any appropriate basis until any occurrence of the first condition. The time extending from the initiation of a phase until an occurrence of the first condition during this phase may be characterized as a first time range for purposes of the first aspect. Using the target pressure to control the velocity increase of a drive ram of the medical fluid injector system may be implemented at any appropriate time during the execution of an injection protocol, including any time after the velocity of the drive ram has actually been decreased for any appropriate reason (e.g., after reaching and/or exceeding the target pressure; after reaching and/or exceeding the target flow rate for an associated phase).

A drive ram velocity may be repeatedly derived on any appropriate basis from at least the target pressure for purposes of the first aspect, and which encompasses both the case where the drive ram velocity is increased in response to such a derivation and where the drive ram velocity in decreased in response to such a derivation. At least one other parameter (e.g., another independent variable) may be used in the derivation of drive ram velocity. For instance, the drive ram velocity (e.g., a dependent variable) may be derived from both the target pressure (e.g., an independent variable) and an actual, operational, or monitored pressure (e.g., an independent variable, and hereafter a "monitored pressure"). A monitored pressure value associated with the operation of a given drive ram may be acquired in any appropriate manner. In one embodiment, a monitored pressure value is derived from both the power being used to advance the drive ram, along with a velocity of the drive ram (where this velocity may be determined in any appropriate manner), Any monitored pressure or monitored pressure value utilized by the first aspect may be associated with a single point in time, or may be an average of monitored pressures or pressure values associated with different points in time (e.g., the monitored pressure could be in the form of a moving average).

A differential between the target pressure and the noted monitored pressure may be used to derive a drive ram velocity value. A drive ram velocity value may be derived in a manner that attempts to reduce the magnitude of an error between the target pressure and the monitored pressure. In one embodiment, at least a two-term controller is used to derive a drive ram velocity value from both the target pressure and an updated monitored pressure value (e.g., using a proportional term and a derivative term). In one embodiment, a PID controller (proportional-integral-derivative controller) is used to derive a drive ram velocity value from both the target pressure and an updated monitored pressure value, although all three terms of such a controller may not in fact be utilized. Any drive ram velocity increase in accordance with the first aspect may be characterized as being recursively derived, iteratively derived, and/or repeatedly derived, including without limitation using a controller of any of the noted configurations.

A second aspect of the present invention is directed to iteratively deriving the velocity of at least one drive ram of a medical fluid injector system, where each such derivation is based upon a target pressure and an actual, operational, or monitored pressure (again, simply a "monitored pressure"), where this iterative derivation is repeated on at least some basis from the beginning of at least one phase of an injection protocol (including where this iterative derivation is undertaken throughout the entirety of one or more phases of the injection protocol), and where a derived velocity is used to advance the associated drive ram during at least one phase of the injection protocol (and thereby including using such a velocity derivation for each phase of an injection protocol). The second aspect may be in the form of a medical fluid injector system that includes both a syringe plunger driver and drive ram motion control logic, where the syringe plunger driver includes both a drive source (e.g., a motor of any appropriate type) and a drive ram (e.g., an axially movable structure), where the drive ram motion control logic is configured to iteratively derive a drive ram velocity for the associated drive ram from both a target pressure and a monitored pressure, where this iterative derivation is undertaken on at least some basis from the beginning of at least one phase of injection protocol and for at least a portion thereof, and where a derived velocity is used to advance the associated drive ram during at least part of at least one phase of the injection protocol. The second aspect may also be in the form of a method of injecting at least one fluid using a medical fluid injector system, where a target pressure is set from data that is input to the medical fluid injector system and that pertains to at least one phase of an injection protocol, where a velocity for a drive ram of the medical fluid injector system is derived from both this target pressure and a monitored pressure from the beginning of at least one phase of the injection protocol and for at least a portion of the execution of at least one phase, and where a derived velocity is used to advance the associated drive ram during the associated phase.

A number of feature refinements and additional features are applicable to the second aspect of the present invention. These feature refinements and additional features may be used individually or in any combination. As such, each of the following features that will be discussed may be, but are not required to be, used with any other feature or combination of features of the second aspect. The following discussion is applicable to the second aspect, up to the start of the discussion of a third aspect of the present invention.

The second aspect may be characterized as being directed to using both a target pressure and a monitored pressure to control how the velocity of at least one drive ram of the medical fluid injector system is increased during at least the initial portion of at least one phase of an injection protocol. The "monitored pressure" used by the second aspect could be associated with a single point in time, or could be an average of monitored pressures or monitored pressure values associated with different points in time (e.g., the "monitored pressure" could be in the form of a moving average, or the average of a certain number of the most recent-in-time monitored pressure values). The second aspect could be implemented to control how the velocity of one or more drive rams of a medical fluid injector system should be increased during any relevant portion of an injection protocol and based upon both the target pressure and the monitored pressure. The second aspect may be used in the execution of any appropriate number of phases of a given injection protocol, and regardless of the number of drive rams being advanced during a given phase (e.g., the target pressure and monitored pressure may be used to control the velocity of a single ram during a given phase; the target pressure and a corresponding monitored pressure may be used to control the velocity of each of multiple drive rams in a given phase—what may be characterized as a simultaneous injection phase). In one embodiment, a single target pressure is associated with the entire injection protocol, regardless of the number of phases (e.g., the same target pressure may be used in relation to each phase of an injection protocol).

The target pressure may be set in response to user input, where this user input is in the form of a value input to the medical fluid injector system in any appropriate manner (e.g., via a data input device of any appropriate type) and at any appropriate location (e.g., from a remote console of the medical fluid injector system; from a powerhead of a power injector of the medical fluid injector system; from a console that is common to both a power injector of the medical fluid injector system, and a scanner or other medical imaging device). A pressure-related prompt (e.g., a prompt for a peak pressure; a prompt for a target pressure) may be presented on one or more displays of the medical fluid injector system at one or more locations. One or more data input devices may be made available to enter a value for a pressure in conjunction with the noted pressure-related prompt. The value for the target pressure could be set to the same value as the value that was input for a peak pressure, or the target pressure could be defined from the value that was input for a peak pressure (e.g., in accordance with an algorithm, such as target pressure=peak pressure minus 25 psi). Any value that is entered for a peak pressure may be characterized as data that may be used to set the target pressure.

Although the velocity of one or more drive rams of the medical fluid injector system could be continually increased throughout at least one phase of an injection protocol and based upon both target pressure and an associated monitored pressure in the case of the second aspect, such need not be the case. The derivation of drive ram velocity in accordance with the second aspect may increase or decrease the velocity of the associated drive ram, or may maintain the current velocity of the associated drive ram. The target pressure and monitored pressure may be collectively used to control the manner in which the velocity of a given drive ram is increased from the time that a particular phase is initiated until some later point in time (e.g., until the target pressure is actually reached; until a target flow rate for an associated phase is reached; until the end of the associated phase). Any appropriate initial velocity may be utilized for purposes of an original derivation of drive ram velocity for a given phase, including a zero velocity. After the velocity of a given drive ram of the medical fluid injector system has been increased for some period of time, the velocity of this drive ram could be maintained at a certain value and/or could actually be reduced based upon both the target pressure and an updated magnitude of the monitored pressure. Any subsequent velocity increase(s) for this drive ram may still be derived from the original target pressure and an updated magnitude of the monitored pressure. The updated magnitude of the monitored pressure could from a single point in time or a single "measurement", or could be an average value (e.g., utilizing a moving average).

Both the target pressure and the monitored pressure may be characterized as being independent variables, while a derived velocity for a given drive ram of the medical fluid injector system may be characterized as being a dependent variable. A drive ram velocity derivation in accordance with the second aspect may be characterized as depending upon and/or being influenced by at least the target pressure and the monitored pressure. In one embodiment, both the target pressure (e.g., a target pressure value) and the monitored pressure (e.g., a monitored pressure value) may be an input to a drive ram motion control algorithm, and the output of this drive ram motion control algorithm may be a drive ram velocity (e.g., a drive ram velocity value). Such a drive ram control algorithm could be executed on any appropriate basis for the iterative derivation contemplated by this second aspect, such as periodically (e.g., every 40 milliseconds, or some other appropriate time period). Although the same target pressure value may be used to derive the drive ram velocity throughout a given phase of an injection protocol, an updated value of the monitored pressure may be used for each such derivation.

The drive ram velocity of at least one drive ram of a medial fluid injector system may be iteratively derived on any appropriate basis throughout an entirety of an injection protocol. Any appropriate timing may be utilized for the drive ram velocity derivations encompassed by the second aspect (e.g., every 40 milliseconds). The derived drive ram velocities may incrementally increase during a given phase until an occurrence of a first condition. This first condition may be the medical fluid injector system reaching the target pressure, reaching a target flow rate for an associated phase, reaching the end of an associated phase, or any combination thereof. In one embodiment, data for the target pressure, a target flow rate, or both may be input to the medical fluid injector system by a user in any appropriate manner (e.g., through a data input device of any appropriate type). The derived drive ram velocity may be initiated at the start of a given phase of an injection protocol and may continue on any appropriate basis until any occurrence of the first condition.

Each monitored pressure value associated with the operation of a given drive ram may be acquired in any appropriate manner in the case of the second aspect. In one embodiment, a monitored pressure value is derived from both the power being used to advance the drive ram, along with a velocity of the drive ram (where this velocity may be measured in any appropriate manner). A differential between the target pressure and the noted monitored pressure may be used to derive a drive ram velocity value. A drive ram velocity value may be derived in a manner that attempts to reduce the magnitude of an error between the target pressure and the monitored pressure. In one embodiment, at least a two-term controller is used to derive a drive ram velocity value from both the target pressure and an updated monitored pressure value (e.g., using a proportional term and a derivative term). In one embodiment, a PID controller (proportional-integral-derivative controller) is used to derive a drive ram velocity value from both the target pressure and an updated monitored pressure value, although all three terms of such a controller may not in fact be utilized. Any drive ram velocity increase in accordance with the second aspect may also be characterized as being recursively derived, including without limitation using a controller of any of the noted configurations.

A third aspect of the present invention is directed to monitoring a pressure associated with an operation of a medical fluid injector system, where a monitored pressure is determined from both a power value being input to a drive source of a syringe plunger driver of the medical fluid injector system, as well as a velocity of a drive ram of this same syringe plunger driver. The third aspect may be in the form of a medical fluid injector system that includes both a syringe plunger driver and pressure monitoring logic, where the syringe plunger driver includes both a drive source (e.g., a motor of any appropriate type) and a drive ram (e.g., an axially movable structure), and where the pressure monitoring logic is configured to derive a monitored pressure from both a power value being input to the drive source and a velocity of the drive ram. The third aspect may also be in the form of a method of injecting at least one fluid using a medical fluid injector system, where at least one syringe plunger driver is operated to advance an associated drive ram to inject at least one fluid into a patient, and where the power being input to the drive source of this syringe plunger driver and the velocity of the associated drive ram (determined in any appropriate manner) are used to derive a monitored pressure. This third aspect may be used in each of the above-noted first and second aspects of the present invention.

A fourth aspect of the present invention is directed to determining a flow rate for each of at least two different drive rams of a medical fluid injector system, where this determination is based upon total flow rate and concentration inputs for at least one phase of an injection protocol where first and second drive rams are simultaneously advanced. The fourth aspect may be in the form of a medical fluid injector system that includes a first syringe plunger driver, a second syringe plunger driver, and flow rate determination logic, where each such syringe plunger driver includes both a drive source (e.g., a motor of any appropriate type) and a drive ram (e.g., an axially movable structure), and where the flow rate determination logic is configured to calculate a flow rate for the drive ram of each of the first and second syringe plunger drivers based upon both a total flow rate input and a concentration input for at least one phase of an injection protocol where the first and second syringe plunger drivers are simultaneously operated (e.g., a phase where two different medical fluids are simultaneously injected into a patient). The fourth aspect may also be in the form of configuring a medical fluid injector system for the simultaneous injection of at least two different medical fluids into a patient, where both a total flow rate and concentration are entered (e.g., input to the medical fluid injector system) for at least one phase of an injection protocol where first and second syringe plunger drivers are simultaneously operated (e.g., a phase where at least two different medical fluids are simultaneously injected into a patient), and where a flow rate for each of first and second drive rams is calculated by the medical fluid injector system based upon both the total flow rate and concentration inputs for the associated phase of the injection protocol.

A number of feature refinements and additional features are applicable to the fourth aspect of the present invention. These feature refinements and additional features may be used individually or in any combination. As such, each of the following features that will be discussed may be, but are not required to be, used with any other feature or combination of features of the fourth aspect. The following discussion is applicable to the fourth aspect, up to the start of the discussion of a fifth aspect of the present invention.

The first syringe plunger driver may be associated with a first medical fluid of any appropriate type (e.g., contrast media), while the second syringe plunger driver may be associated with a second medical fluid of any appropriate type (e.g., saline), but which is different in at least some respect from the first medical fluid. The noted concentration input may relate the relative amounts of the first and second medical fluids to be simultaneously injected. The concentration input may be expressed in any appropriate manner, for instance in the form of a percentage. In one embodiment, a concentration input of "30%" may mean that in a phase of an injection protocol where the first and second drive rams are being simultaneously advanced, 30% of the total volume to be injected during such a phase will be defined by the first medical fluid and 70% of this same total volume will be defined by the second medical fluid.

The total flow rate and concentration inputs each may be in the form of user input. A user may input both the desired total flow rate and the desired concentration for a given phase into the medical fluid injector system in any appropriate manner (e.g., via a data input device of any appropriate type) and at any appropriate location (e.g., from a remote console of the medical fluid injector system; from a powerhead of a power injector of the medical fluid injector system; from a console that is common to both a power injector of the medical fluid injector system, and a scanner or other medical imaging device). A total flow rate prompt and a concentration prompt for at least one phase may be presented on at least one display of the medical fluid injector system, including where the total flow rate and concentration prompts for a given phase are simultaneously presented on two or more displays. One or more data input devices may be made available to enter the desired total flow rate and concentration for a given phase in conjunction with the corresponding prompts.

It should be appreciated that the fourth aspect may be used in conjunction with two or more phases of an injection protocol where multiple drive rams are simultaneously advanced. It should also be appreciated that the fourth aspect may be used in conjunction with each phase of an injection protocol where multiple drive rams are simultaneously advanced. This fourth aspect may be used in combination with each of the above-noted first and second aspects of the present invention.

A fifth aspect of the present invention is directed to determining an injection volume for each of at least two different drive rams of a medical fluid injector system, where this determination is based upon total injection volume and concentration inputs for at least one phase of an injection protocol where first and second drive rams are simultaneously advanced. The fifth aspect may be in the form of a medical fluid injector system that includes a first syringe plunger driver, a second syringe plunger driver, and injection volume determination logic, where each such syringe plunger driver includes both a drive source (e.g., a motor of any appropriate type) and a drive ram (e.g., an axially movable structure), and where the injection volume determination logic is configured to calculate an injection volume for the drive ram of each of the first and second syringe plunger drivers based upon both a total injection volume input and a concentration input for at least one phase of an injection protocol where the first and second syringe plunger drivers are simultaneously operated (e.g., a phase where two different medical fluids are simultaneously injected into a patient). The fifth aspect may also be in the form of configuring a medical fluid injector system for the simultaneous injection of at least two different medical fluids into a patient, where both a total injection volume and concentration are entered (e.g., input to the medical fluid injector system) for at least one phase of an injection protocol where first and second syringe plunger drivers are simultaneously operated (e.g., a phase where at least two different medical fluids are simultaneously injected into a patient), and where an injection volume for each of first and second drive rams is calculated by the medical fluid injector system based upon both the total injection volume and concentration inputs for the associated phase of the injection protocol.

A number of feature refinements and additional features are applicable to the fifth aspect of the present invention. These feature refinements and additional features may be used individually or in any combination. As such, each of the following features that will be discussed may be, but are not required to be, used with any other feature or combination of features of the fifth aspect. The following discussion is applicable to the fifth aspect, up to the start of the discussion of a sixth aspect of the present invention.

The first syringe plunger driver may be associated with a first medical fluid of any appropriate type (e.g., contrast media), while the second syringe plunger driver may be associated with a second medical fluid of any appropriate type (e.g., saline), but which is different in at least some respect from the first medical fluid. The noted concentration input may relate the relative amounts of the first and second medical fluids to be simultaneously injected. The concentration input may be expressed in any appropriate manner, for instance in the form of a percentage. In one embodiment, a concentration input of "30%" may mean that in a phase of an injection protocol where the first and second drive rams are being simultaneously advanced, 30% of the total volume to be injected during such a phase will be defined by the first medical fluid and 70% of this same total volume will be defined by the second medical fluid.

The total injection volume and concentration inputs each may be in the form of user input. A user may input both the desired total injection volume and the desired concentration for a given phase into the medical fluid injector system in any appropriate manner (e.g., via a data input device of any appropriate type) and at any appropriate location (e.g., from a remote console of the medical fluid injector system; from a powerhead of a power injector of the medical fluid injector system; from a console that is common to both a power injector of the medical fluid injector system, and a scanner or other medical imaging device).

The medical fluid injector system may include at least one display. A given display may be disposed at any appropriate location (e.g., inside/outside of an imaging suite). Multiple displays may be utilized and disposed in any appropriate arrangement (e.g., incorporated by remote console (of the medical fluid injector system) located outside of an imaging suite, incorporated by a powerhead of a power injector (of the medical fluid injector system) located within an imaging suite; incorporated by a common console for a scanner or other medical imaging device and a power injector (of the medical fluid injector system) that is located within the imaging suite). A total injection volume prompt and a concentration prompt for at least one phase may be presented on at least one display of the medical fluid injector system, including where the total injection volume and concentration prompts for a given phase are simultaneously presented on two or more displays. One or more data input devices may be made available to enter the desired total injection volume and concentration for a given phase in conjunction with the corresponding prompts.

It should be appreciated that the fifth aspect may be used in conjunction with two or more phases of an injection protocol where multiple drive rams are simultaneously advanced. It should also be appreciated that the fifth aspect may be used in conjunction with each phase of an injection protocol where multiple drive rams are simultaneously advanced. This fifth aspect may be used in combination with each of the above-noted first, second, and fourth aspects of the present invention.

A sixth aspect of the present invention is directed to presenting at least one multi-color graphic on at least one display of a medical fluid injector system, where color amounts in such a multi-color graphic are correlated with a concentration for a phase of an injection protocol where first and second syringe plunger drivers of the medical fluid injector system are simultaneously operated. The sixth aspect may be in the form of a medical fluid injector system that includes first and second syringe plunger drivers, at least one display, and display control logic, where the display control logic includes a programmed concentration variable, and where the display control logic is configured to present at least one multi-color graphic on at least one display and correlate an amount of colors in such a multi-color graphic with a value of the programmed concentration variable for at least one phase of an injection protocol where the first and second syringe plunger drivers are simultaneously operated. The sixth aspect may also be in the form of a method of operation for a medical fluid injector system, where a concentration value is input to the medical fluid injector system, where first and second drive rams of the medical fluid delivery system are simultaneously advanced, where at least one multi-color graphic is presented on at least one display for at least one phase of an injection protocol where the first and second drive rams are simultaneously advanced, and where the amount of colors included in such a multi-color graphic is correlated with the concentration value.

A number of feature refinements and additional features are applicable to the sixth aspect of the present invention. These feature refinements and additional features may be used individually or in any combination. As such, each of the following features that will be discussed may be, but are not required to be, used with any other feature or combination of features of the sixth aspect. The following discussion is applicable to at least the sixth aspect of the present invention.

A concentration value or a value for a programmed concentration variable may be in the form of user input. The medical fluid injector system may include at least one data input device of any appropriate type. A concentration value or a value for a programmed concentration variable may be entered through any such data input device.

A concentration value or a value for a programmed concentration variable may relate the total amount of a first medical fluid and the total amount of a second medical fluid to be simultaneously injected during a phase of an injection protocol where the first and second syringe plunger drivers are simultaneously operated. The first and second medical fluids, that are simultaneously injected during a phase of an injection protocol where the first and second syringe plunger drivers are simultaneously operated, may be of any appropriate type (e.g., contrast media, saline).

First and second colors may be utilized by a given multi-color graphic. The first color may be associated with a quantity of a first medical fluid to be injected during a phase of an injection protocol where the first and second syringe plunger drivers are simultaneously operated, and in accordance with the concentration value or the to value for a programmed concentration variable. The second color may be associated with a quantity of a second medical fluid to be injected during a phase of an injection protocol where the first and second syringe plunger drivers are simultaneously operated, and in accordance with the concentration value or the value for a programmed concentration variable.

The amount of the first color included in a given multi-color graphic may be proportional to the quantity of a first medical fluid to be injected during a phase of an injection protocol where the first and second syringe plunger drivers are simultaneously operated (e.g., and in accordance with the concentration value or the value for a programmed concentration variable). The amount of the second color included in a given multi-color graphic may be proportional to the quantity of a second medical fluid to be injected during a phase of an injection protocol where the first and second syringe plunger drivers are simultaneously operated (e.g., and in accordance with the concentration value or the value for a programmed concentration variable).

An amount of the first color included in a given multi-color graphic may increase with an increase in a magnitude of the concentration value or the value for a programmed concentration variable, whereas an amount of the second color included in a given multi-color graphic may decrease with an increase in a magnitude of the concentration value or the value for a programmed concentration variable. An amount of the first color included in a given multi-color graphic may decrease with a decrease in a magnitude of the concentration value or the value for a programmed concentration variable, whereas an amount of the second color included in a given multi-color graphic may increase with a decrease in a magnitude of the concentration value or the value for a programmed concentration variable.

The amount of colors in a given multi-color graphic may convey a concentration of a first medical fluid relative to a second medical fluid for a phase of an injection protocol where the first and second syringe plunger drivers are simultaneously operated. Consider the case of a first multi-color graphic. This first multi-color graphic not only may convey concentration information based upon amounts of a plurality of colors incorporated by such a first multi-color graphic, but the first multi-color graphic may also numerically convey concentration information. More than one multi-color graphic may be simultaneously presented on a display and convey the same concentration information. Each multi-color graphic, other than the noted first multi-color graphic, may numerically convey information on other parameters (i.e., other than concentration) associated with the operation of the medical fluid injector system. For instance, a given multi-color graphic for a particular phase could numerically convey information on flow rate, total injection volume, and which of the first and second syringe plunger drivers are being operated. Each multi-color graphic that is simultaneously presented on at least one display may provide the same concentration information via a relative amount of multiple colors, and each such multi-color graphic may also numerically convey information on different parameters associated with the operation of the medical fluid injector system.

A seventh aspect of the present invention is directed to providing control over whether one or both of an inject delay graphic and scan delay graphic is displayed to an operator of a medical fluid injector system. An "inject delay" may be characterized as a delay (typically in seconds) from the time an operator initiates an injection, until the injection as described by the programmed injection protocol actually begins. A "scan delay" may be characterized as a delay (typically in seconds) from the time the operator initiates an injection until image acquisition operations are initiated with the imaging device. In any case, the seventh aspect may be in the form of a medical fluid injector system that includes at least one syringe plunger driver, at least one display, at least one data input device, and at least one screen presented on at least one display of the system that provides an option as to whether or not an inject delay graphic, a scan delay graphic, or both should be presented on at least one display when programming an injection protocol for the medical fluid injector, during execution of an injection protocol, or both. The seventh aspect may also be in the form of a method of operation for a medical fluid injector system, where a screen is presented on at least one display of the medical fluid injector system that allows a user to select whether or not an inject delay graphic, a scan delay graphic, or both should thereafter be presented on at least one display of the medical fluid injector system when programming an injection protocol, during execution of an injection protocol, or both. The inject delay graphic may be used to program an injection delay into an injection protocol, to display a programmed injection delay, or both. The scan delay graphic may be used to program a scan delay into an injection protocol, to display a programmed scan delay, or both.

A number of feature refinements and additional features are separately applicable to each of above-noted first, second, third, fourth, fifth, sixth, and seventh aspects of the present invention. These feature refinements and additional features may be used individually or in any combination in relation to each of the above-noted first, second, third, fourth, fifth, sixth aspects, and seventh aspects.

The present invention may utilize one or more displays. A given display may be disposed at any appropriate location (e.g., inside/outside of an imaging suite). Multiple displays may be utilized and disposed in any appropriate arrangement (e.g., incorporated by remote console located outside of an imaging suite; incorporated by a powerhead of a power injector located within an imaging suite; incorporated by a common console for a scanner and a power injector that is located within the imaging suite).

The present invention may utilize one or more data input devices of any appropriate type. Each such data input device may be at any appropriate location (e.g., outside of an imaging suite, inside an imaging suite). Each such data input device may be associated with any appropriate component or combination of components (e.g., a remote console associated with a power injector; a powerhead of a power injector; a common console for a scanner and power injector).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time, One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical imaging application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging) and/or any appropriate medical diagnostic and/or therapeutic application (e.g., injection of chemotherapy, pain management, etc.). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, therapeutic fluid, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injectors syringe plunger drive assembly such that the syringe plunger drive assembly is able to advance the plunger in at least one direction, and possibly in two different, opposite directions.

Any "logic" that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This logic may be implemented at any single location or at multiple locations that are interconnected in any appropriate manner (e.g., via any type of network).

Any feature of the present invention that is intended to be limited to a "singular" context or the like will be clearly set forth herein by terms such as "only," "single," "limited to," or the like, Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical). Finally, a reference of a feature in conjunction with the phrase "in one embodiment" does not limit the use of the feature to a single embodiment.

BRIEF DESCRIPTION OF THE FIGURES

FIG. 3A is a schematic of an embodiment of an imaging suite that utilizes both a medical fluid injector system and an imaging system.

DETAILED DESCRIPTION

Figure 1:
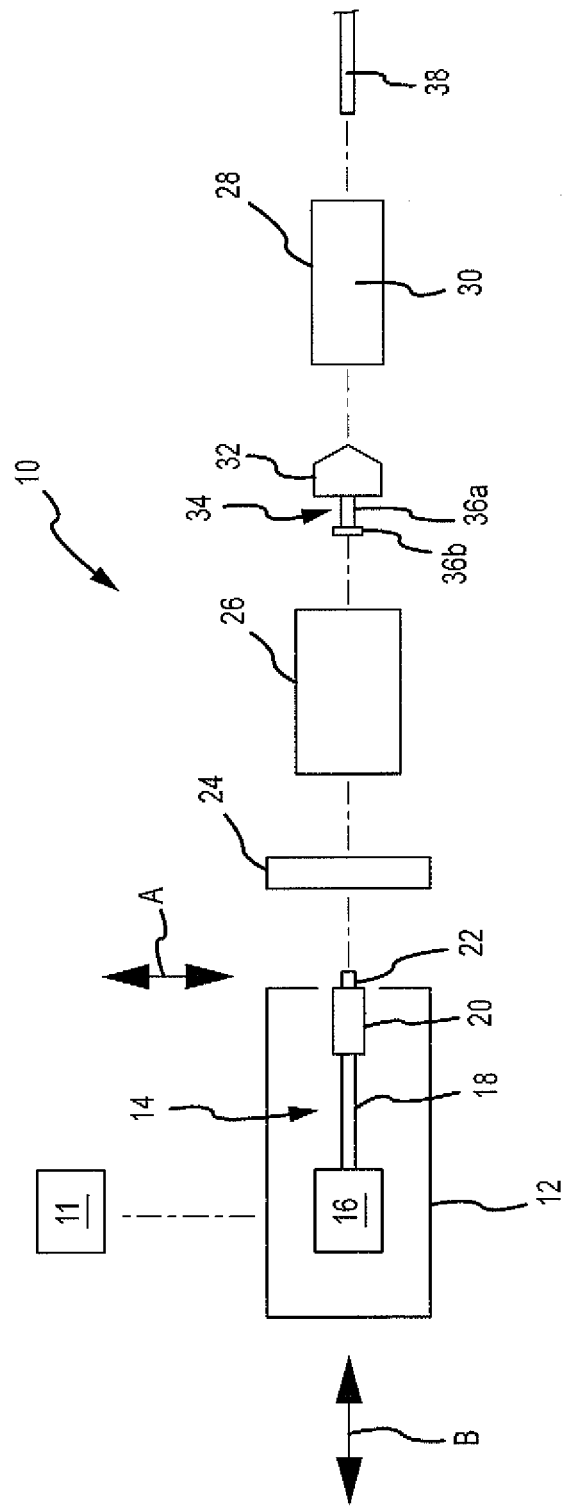
FIG. 1 is a schematic of an embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12 (e.g., a remote console; a common console for the power injector 12 and an imaging device), and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A drive ram or ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b, However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe to plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed an the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
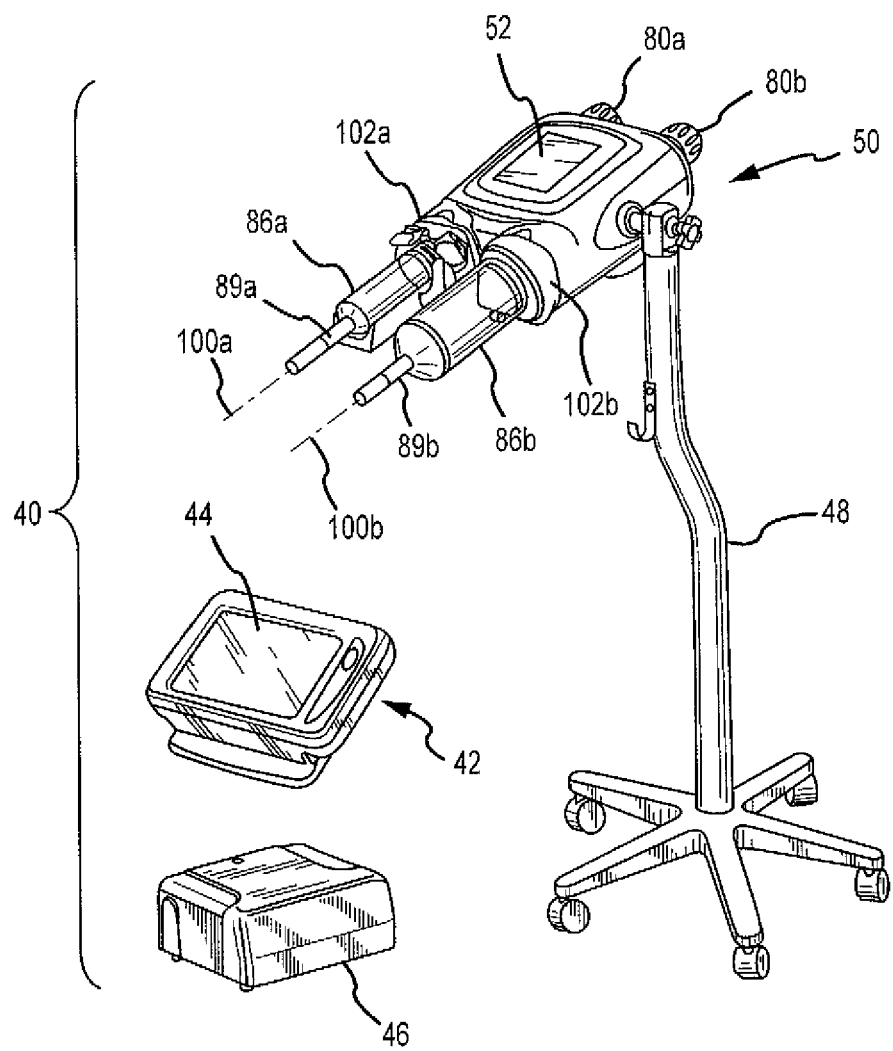
FIG. 2A is a perspective view of an embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. Two syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
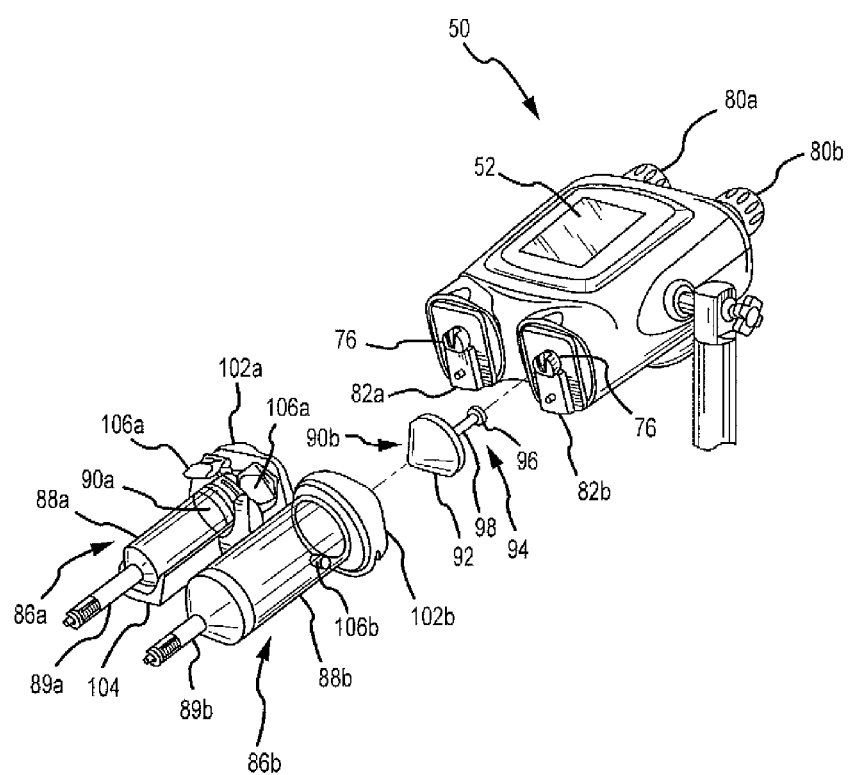
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2O. Generally, the ram coupler 76 may be coupled with the syringe plunger 90a of the syringe 86a, and the ram coupler 76 and ram 74 (FIG. 2O) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 20), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A), It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
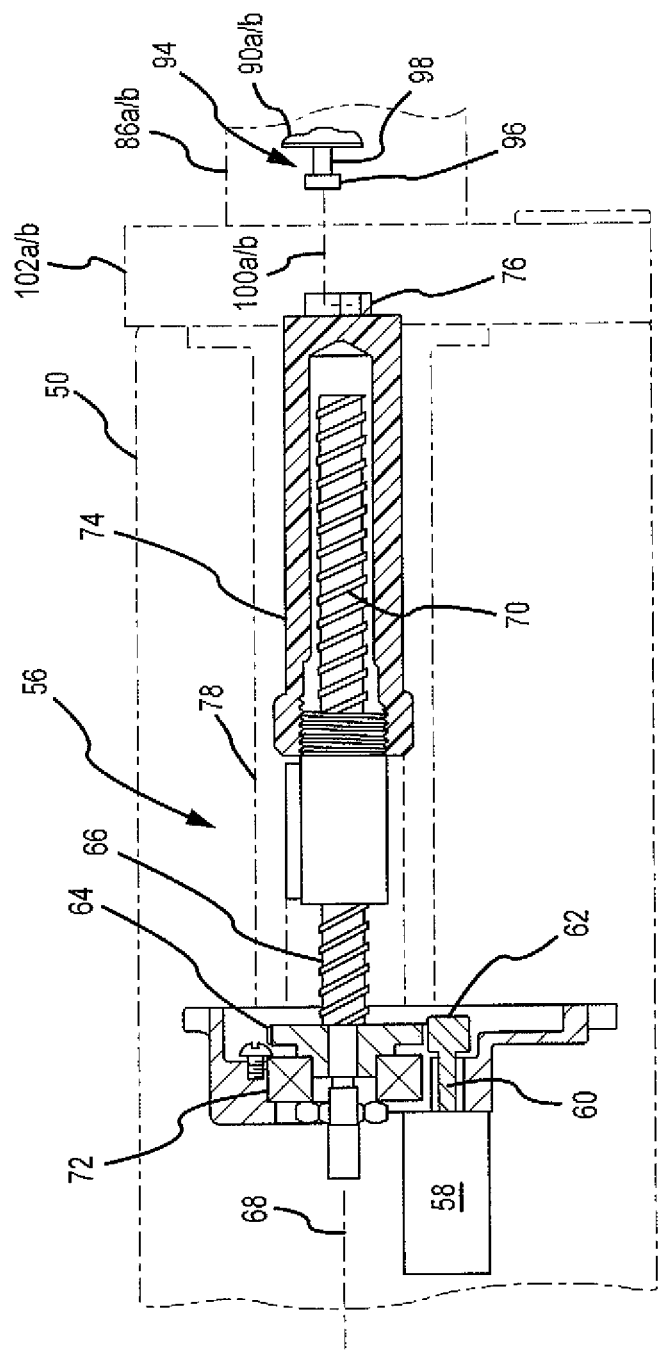
FIG. 2C is a schematic of an embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a drive source or motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or drive ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 to provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 20 illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient) and/or any appropriate medical diagnostic and/or therapeutic application (e.g., injection of chemotherapy, pain management, etc.). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, therapeutic fluid, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

FIG. 3A schematically presents one embodiment of what may be characterized as an imaging suite 400. In the illustrated embodiment, the imaging suite 400 includes a control room 402 and an imaging room 420 that are separated by an appropriate barrier 412. This separation may not be required in all instances. In some embodiments, this barrier 412 may include radiation (e.g., alpha, beta and/or gamma) shielding, RF shielding, and/or any other type of material that may reduce the likelihood of undesired conditions that could hinder image acquisition.

The imaging suite 400 includes a medical fluid or contrast media injector system 430. The contrast media injector system 430 includes a power injector 432 (e.g., power injector 10; power injector 40) and a remote console 404. The power injector 432 is operatively connected with the remote console 404, may be operatively connected with an imaging device 422 (discussed below), and is fluidly connectable with a patient 424 (e.g., such that the power injector 432 may inject contrast media into the patient 424). The power injector 432 may include a display 434 and at least one user input device 436 of any appropriate type (e.g., a keyboard, mouse, touch screen, joystick, trackball, or the like). Both the display 434 and one or more of such user input devices 436 may be associated with a powerhead of the power injector 432.

The remote console 404 (e.g., a computer) of the contrast media injector system 430 may be located in the control room 402, Components of the remote console 404 include a remote console display 406 and at least one user input device 408, Each user input device 408 of the injector system 430 may be of any appropriate type, for instance, in the form of a keyboard, mouse, touch screen, joystick, trackball, or the like. The remote console 404 is operatively interconnected with the power injector 432 by a communication link 410 of any appropriate type. Generally, a user may program injection parameters for the power injector 432 (e.g., define an injection protocol, for instance one or more phases and where each phase includes injection parameters such as a volume of contrast media to be injected and an injection flow rate, along with possibly one or more injection delays (e.g., a hold or a pause)) through the user input device 408 of the remote console 404.

The imaging suite 400 also includes a medical imaging system 407. The medical imaging system 407 includes a remote console 409 and an imaging device 422. The imaging device 422 may be of any appropriate size, shape, configuration, and/or type, and its image-acquisition functionality may utilize any appropriate technology or combination of technologies. In one embodiment, the imaging device 422 is in the form of a CT scanner.

The remote console 409 (e.g., a computer) of the medical imaging system 407 may be located in the control room 402. Components of the remote console 409 may include a remote console display 411 and at least one user input device 413. Each user input device 413 of the medical imaging system 407 may be of any appropriate type, for instance, in the form of a keyboard, mouse, touch screen, joystick, trackball, or the like. The remote console 409 of the imaging system 407 is operatively interconnected with the imaging device 422 by a communication link 415 of any appropriate type. Generally, a user may program imaging parameters for the imaging device 422 and/or control (e.g., initiate and/or terminate) imaging procedures by way of the user input device 413 of the remote console 409.

The medical imaging system 407 (e.g., the remote console 409 thereof) may be operatively connected with the contrast media injector system 430 (e.g., the remote console 404 thereof). In the case where the imaging system 407 is indeed operatively connected with the injector system 430, some embodiments allow for a user to program injection parameters and/or control (e.g., initiate and/or terminate) injection procedures for the power injector 432 through the user input device 413 of the imaging system's remote console 409 in addition to the performing the programming and/or control functionalities herein-described with regard to the imaging device 422. In some embodiments of the imaging suite 400, the injector system 430 and the medical imaging system 407 may only include a single, shared remote console (not shown) from which a user may perform any of the herein-described program and/or control operations for both the imaging device 422 and the power injector 432.

Figure 3B:
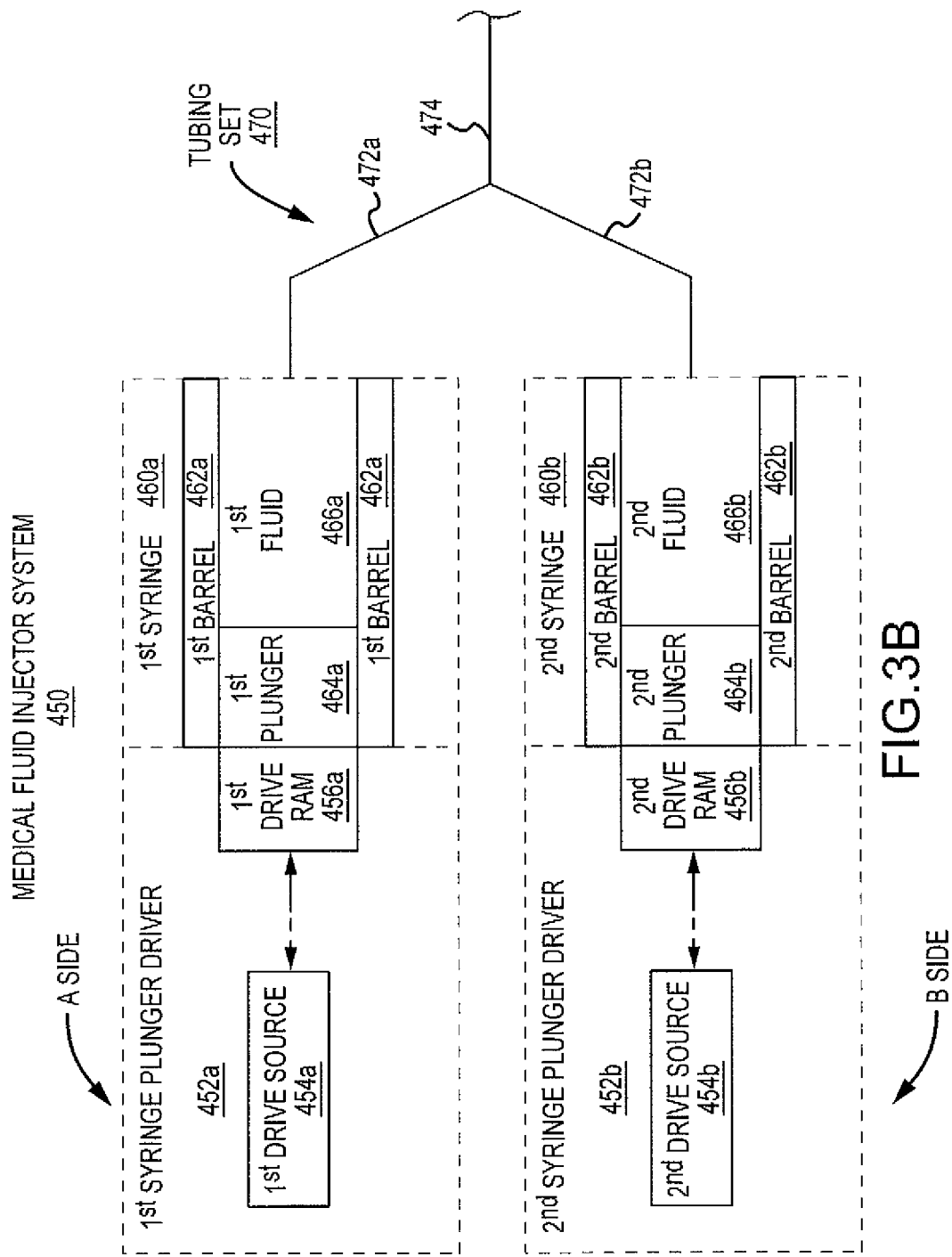
FIG. 3B is a schematic of a dual head medical fluid injector system that may be used to simultaneously inject two medical fluids.

Various protocols to be described herein may be particularly relevant to what may be characterized as a dual head injector. The contrast media injector system 430 of FIG. 3A may utilize such a dual head injector (e.g., the power injector 432 in FIG. 3A may be in the form of a dual head injector). A schematic of a medical fluid injector system that is able to separately or simultaneously inject two different medical fluids is illustrated in FIG. 3B and is identified by reference numeral 450. The medical fluid injector system 450 includes both an "A" side (e.g., one head) and a "B" side (e.g., another head). The A and B sides of the medical fluid injector system 450 may be incorporated by a common powerhead (e.g., powerhead 50) of a power injector (e.g., power injector 40) to define a dual head configuration.

The A side of the medical fluid injector system 450 includes a first syringe plunger driver 452a and a first syringe 460a. The first syringe plunger driver 452a includes a first drive source 454a that is able to move a first drive ram 456a along an axial path in at least a first direction associated with a discharge stroke, although the first drive source 454a could move the first drive ram 456a in each of first and second directions along such an axial path. Similarly, the second syringe plunger driver 452b includes a second drive source 454b that is able to move a second drive ram 456b along an axial path in at least a first direction associated with a discharge stroke, although the second drive source 454b could move the second drive ram 456b in each of first and second directions along such an axial path.

A first syringe 460a is associated with the A side of the medical fluid injector system 450. This first syringe 460a includes a first syringe barrel 462a, along with a first syringe plunger 464a that is disposed within the first syringe barrel 462a. A first outlet leg 472a of a tubing set 470 is fluidly connected with a discharge port(s) of the first syringe 460a. Similarly, a second syringe 460b is associated with the B side of the medical fluid injector system 450. This second syringe 460b includes a second syringe barrel 462b, along with a second syringe plunger 464b that is disposed within the second syringe barrel 462b. A second outlet leg 472b of the tubing set 470 is fluidly connected with a discharge port(s) of the first syringe 460a. In the illustrated embodiment, the first outlet leg 472a and the second outlet leg 472b of the tubing set 470 merge into a common discharge leg 474.

A first medical fluid 466a (e.g., contrast media) is contained within the first syringe barrel 462a. Operation of the first syringe plunger driver 452a advances the first drive ram 456a relative to the first syringe barrel 462a, and which in turn advances the first syringe plunger 464a relative to the first syringe barrel 462a to discharge first medical fluid 466a from the first syringe 460a into the tubing set 470. Similarly, a second medical fluid 466b (e.g., saline) is contained within the second syringe barrel 462b. Operation of the second syringe plunger driver 452b advances the second drive ram 456b relative to the second syringe barrel 462b, and which in turn advances the second syringe plunger 464b relative to the syringe barrel 462b to discharge second medical fluid 466b from the second syringe 460b into the tubing set 470.

It should be appreciated that the medical fluid injector system 450, as presented in FIG. 3B, may be used to separately inject first medical fluid 466a into a patient at a common injection site (e.g., via operation of the first syringe plunger driver 452a, and while not operating the second syringe plunger driver 452b), to separately inject second medical fluid 466b into the patient at this same common injection site (e.g., via operation of the second syringe plunger driver 452b, and while not operating the first syringe plunger driver 452a), and to simultaneously first medical fluid 466a and second medical fluid 466b into the patient at this same common injection site (e.g., via simultaneous operation of the first syringe plunger driver 452a and the second syringe plunger driver 452b). Other tubing sets could be used with the medical fluid injector system 450, and where the syringe plunger drivers 452a, 452b could either be individually operated or simultaneously operated.

Figure 3C:
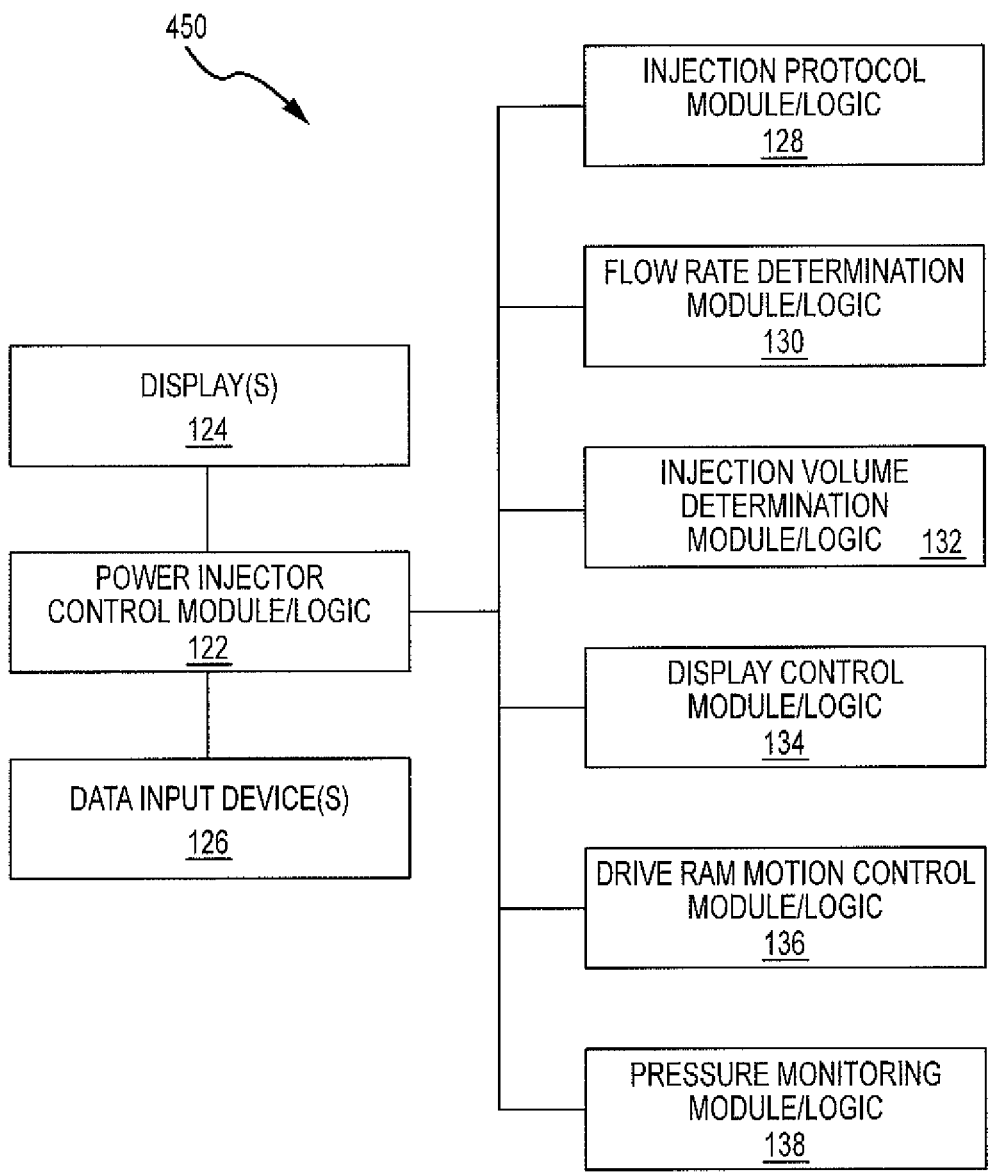
FIG. 3C is a schematic of an embodiment of a power injector control module/logic that may be used by the medical fluid injector system of FIG. 3B.

FIG. 3C schematically illustrates one embodiment of a power injector control module/logic 122 for the medical fluid injector system 450 of FIG. 3B, but which may be utilized by any appropriate power injector or any appropriate medical fluid injector system, including without limitation the power injector 10 of FIG. 1, the power injector 40 of FIGS. 2A-C, and the medical fluid injector system 430 of FIG. 3A. One or more user or data input devices 126 of any appropriate configuration and/or type (e.g., in accordance with the embodiment of FIG. 3A) may be operatively interconnected with the power injector control module/logic 122. Multiple data input devices 126 may be utilized and may be disposed in any appropriate location (e.g., in the control room 402, for instance as part of the remote console 404; in the imaging room 420). A given data input device 126 could communicate with not only the medical fluid injector system 450, but an imaging system as well (e.g., imaging system 407, for instance via a common control console that communicates with each of a medical fluid injector system and an imaging system).

One or more displays 124 of any appropriate configuration and/or type may also be operatively interconnected with the power injector control module/logic 122. Multiple displays 124 may be utilized and may be disposed in any appropriate location (e.g., in the control room 402, for instance as part of the remote console 404; in the imaging room 420, for instance as part of a powerhead that includes the A and B sides of the medical fluid injector system 450). A given display 124 may be associated with not only the medical fluid injector system 450, but an imaging system as well (e.g., imaging system 407, for instance via a common control console that communicates with each of a medical fluid injector system and an imaging system). One or more of the displays 124 may utilize touch screen functionality.

In the illustrated embodiment, the power injector control module/logic 122 of FIG. 3C includes an injection protocol module/logic 128, a flow rate determination module/logic 130, an injection volume determination module/logic 132, a display control module/logic 134, a drive ram motion control module/logic 136, and a pressure monitoring module/logic 138. Representative protocols/configurations that may be utilized by each of the modules illustrated in FIG. 3C will be discussed in more detail below, Other modules may be used by the power injector control module/logic 122. For instance, the medical fluid injector system 450 may include a module that includes one or more injection protocols that have been previously programmed and stored on an appropriate computer-readable storage medium (e.g., a library or data store of injection protocols that may be run by the medical fluid injector system 450). Such a module may communicate with and/or be part of the power injector control module/logic 122. An injection protocol may include one or more programmed phases. Each phase of an injection protocol may include injection parameters such as a total amount of fluid to be injected and an injection flow rate, as well as possibly one or more injection delays (sometimes referred to as "holds" and/or "pauses") and each of which can be of finite or infinite duration. A phase of an injection protocol may be directed to injecting a single liquid at a single injection site. A phase of an injection protocol may be directed to simultaneously injecting multiple fluids (e.g., contrast media and saline) at a single injection site. An injection protocol may include one or more phases that are programmed in any appropriate manner.

Other programmed protocols may be utilized by the power injector control module/logic 122 of FIG. 3C, for instance a module that includes one or more OptiBolus® protocols, a module that includes one or more Timing Bolus® protocols, and a module that includes one or more drip mode protocols. Generally, an OptiBolus® protocol may be configured to deliver an exponentially decaying flow rate injection that optimizes the contrast usage and provides an extended period of uniform enhancement of the area of interest. A Timing Bolus® injection protocol may be configured to provide a timing bolus injection—a small volume of contrast media, followed by a small volume of saline—to a patient for purposes of determining the optimal scan delay needed to capture the contrast media in the area of interest. A drip mode protocol may be configured to provide a drip injection—a low flow rate injection of a small volume of saline delivered to the patient to keep open the fluid pathway from the power injector to the patient.

A given power injector control module/logic 122 may utilize any one or more of the above-noted modules/logics and in any appropriate combination. It should be appreciated that the manner in which the power injector control module/logic 122 implements one or more of the above-noted functionalities, as well as those addressed hereafter, is not of particular importance. Any configuration or arrangement may be utilized for the power injector control module/logic 122 to provide any one or more of these functionalities.

Figure 4:
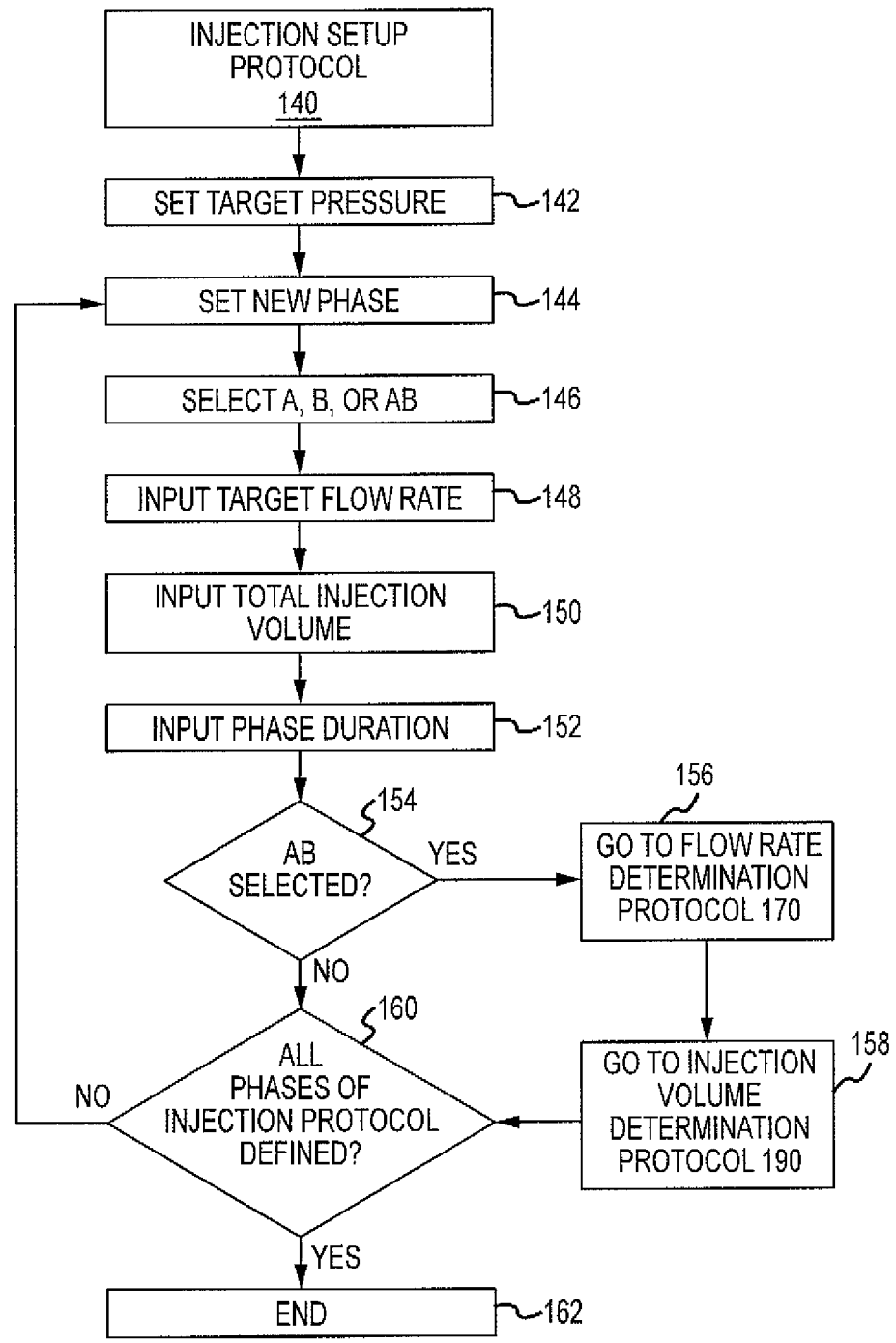
FIG. 4 is a schematic of an embodiment of an injection setup protocol that may be used by a medical fluid injector system.

One embodiment of an injection setup protocol that may be used by the injection protocol module/logic 128 (FIG. 3C) is illustrated in FIG. 4 and is identified by reference numeral 140. An injection protocol to be executed by the medical fluid injector system 450 may be programmed into the medical fluid injector system 450 in accordance with the injection setup protocol 140. Step 142 of the protocol 140 of FIG. 4 is directed to setting a target pressure. In the illustrated embodiment, a single target pressure may be set for the injection protocol that is being programmed, regardless of how many phases are to be utilized by the injection protocol (e.g., the same target pressure may apply to each phase of an injection protocol). Generally, the target pressure that is set pursuant to step 142 may be used to control the operation of the medical fluid injector system 450, for instance the velocity at which one or both drive rams 456a, 456b of the medical fluid injector system 450 are advanced. This will be discussed in more detail below in relation to the drive ram motion control protocol 270 of FIG. 8.

The target pressure associated with step 142 may coincide with a programmed value provided by a user (e.g., input to the medical fluid injector system 450 by a user through a peak pressure icon 212 that will be discussed in more detail below regarding one or more screens that may be used by the medical fluid injector system 450—FIGS. 10-13). That is, if a user programs an injection protocol to have a peak pressure of 325 psi, the target pressure for step 142 could also be set at 325 psi. However, the target pressure associated with step 142 could be derived on any appropriate basis from a value that a user has programmed as a peak pressure. For instance, the target pressure could be determined by an algorithm that uses a programmed peak pressure as an input (e.g., target pressure=peak pressure minus 25 psi (or any other appropriate value)).

Any appropriate number of phases may be defined by the injection setup protocol 140. A phase to be defined for the injection protocol may be set in any appropriate manner pursuant to step 144, and may be defined as follows. Steps 146, 148, 150, and 152 may be executed in any appropriate order. Step 146 is directed to selecting whether the phase currently being defined is to be associated with operation of only the A side of the medical fluid injector system 450 (identified by an "A" designation in step 146), with operation of only the B side of the medical fluid injector system 450 (identified by a "B" designation in step 146), or with simultaneous operation of the A and B sides of the medical fluid injector system 450 (identified by an "AB" designation in step 146). Other parameters for the phase that may be defined through the protocol 140 include without limitation: 1) inputting the target flow rate to the medical fluid injector system 450 pursuant to step 148; 2) inputting the total injection volume to the medical fluid injector system 450 pursuant to step 150; and 3) inputting the duration for the phase to the medical fluid injector system 450 pursuant to step 152.

In the event that a simultaneous injection phase was selected through execution of step 146 (i.e., "AB" was selected pursuant to step 146), the protocol 140 proceeds from step 154 to steps 156 and 158. Step 156 and step 158 may be executed in any appropriate order. Step 156 is directed to the execution of a flow rate determination protocol 170 that will be discussed in more detail below in relation to FIG. 5, but which is generally directed to how the flow rates for the A side and B side of the medical fluid injector system 450 are determined for a simultaneous injection phase. Step 158 is directed to execution of an injection volume determination protocol 190 that will be discussed in more detail below in relation to FIG. 6, but which is generally directed to how the injection volumes for the A side and B side of the medical fluid injector system 450 are determined for a simultaneous injection phase. It should be appreciated that the injection setup protocol 140 (FIG. 4), as well as the flow rate determination protocol 170 (FIG. 5) and the injection volume determination protocol 190 (FIG. 6), may be configured to avoid duplicate execution of steps.

Each of the various parameters that are entered pursuant to the injection setup protocol 140 of FIG. 4 for a particular phase (e.g., the operational drive ram(s) 456a, 456b (step 146), target flow rate (step 148), total injection volume (step 150), and phase duration (152)) may be characterized as user inputs. Any appropriate data input device 126 of the medical fluid injector system 450 may be used to input or enter each such parameter. In any case and after the relevant parameters of a given phase have been defined in accordance with the foregoing, a determination may be made pursuant to step 160 as to whether all desired phases for the injection protocol have been defined through execution of the injection setup protocol 140. If not, the injection setup protocol 140 returns to step 144 for repetition in accordance with the foregoing. Otherwise, the protocol 140 may be terminated pursuant to step 162.

Figure 5:
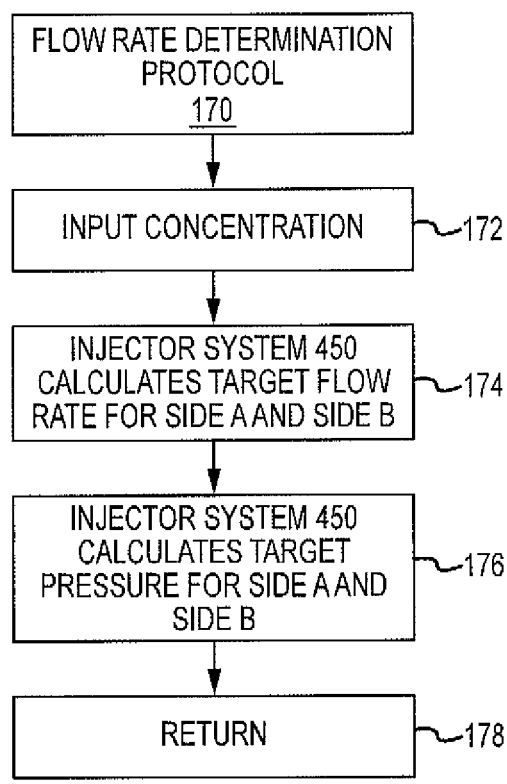
FIG. 5 is a schematic of an embodiment of a flow rate determination protocol that may be used by a medical fluid injector system.

One embodiment of a flow rate determination protocol that may be used by the flow rate determination module/logic 130 (FIG. 3C) is illustrated in FIG. 5 and is identified by reference numeral 170. As previously noted, the flow rate determination protocol 170 may be executed pursuant to step 156 of the injection setup protocol 140 (FIG. 4). In any case, the flow rate determination protocol 170 may be executed for the case where a phase of an injection protocol being programmed involves a simultaneous injection of multiple fluids (e.g., a simultaneous injection phase). Step 148 of the injection setup protocol 140 again is directed to inputting a target flow rate. The target flow rate that is entered pursuant to step 148 should be the total flow rate that is desired to be injected into the patient in a simultaneous injection configuration (e.g., where both the A side and B side of an medical fluid injector system 450 are simultaneously operated to simultaneously inject the first fluid 466a and the second fluid 466b into a patient). Data from step 148 of the injection setup protocol 140 may be used by the flow rate determination protocol 170 of FIG. 5, or the flow rate determination protocol 170 could be configured to independently acquire data on the total target flow rate.

The concentration for the simultaneous injection phase being defined may be input to the medical fluid injector system 450 pursuant to step 172 of the flow rate determination protocol 170. Step 172 may be executed any time after an "AB" designation was selected pursuant to step 146 of the injection setup protocol 140. In any case, any appropriate format may be utilized for inputting the concentration. Generally, the concentration relates the relative amounts of the first fluid 466a second fluid 466b that are to be simultaneously injected pursuant to the phase being defined. In one embodiment, the concentration may be input in the form of a number which is identified as a percentage of the amount of the first fluid 466a that is to be injected in the subject phase relative to the total amount of the first fluid 466a and the second fluid 466b that are to be simultaneously injected in this phase.

Pursuant to step 174 of the flow rate determination protocol 170, the medical fluid injector system 450 calculates the target flow rate for its A side (e.g., the speed at which the drive ram 456a needs to be advanced to realize its target flow rate—the flow rate of the first fluid 466a that is discharged from the first syringe 460a by operation of the first syringe plunger driver 452a) from both the target flow rate (step 148 of the injection setup protocol 140) and the concentration (step 172 of the flow rate determination protocol 170), and further calculates the target flow rate for its B side (e.g., the speed at which the drive ram 456b needs to be advanced to realize its target flow rate—the flow rate of the second fluid 466b that is discharged from the second syringe 460b by operation of the second syringe plunger driver 452b) from both the total target flow rate (step 148 of the injection setup protocol 140) and the concentration (step 172 of the flow rate determination protocol 170).

In certain instances, the target flow rates for the A and B sides of the injector system 450 will simply be the corresponding percentage of the concentration (step 172 of the flow rate determination protocol 140), multiplied by the total target flow rate (step 148 of the injection setup protocol 140). For instance, if the total target flow rate from step 148 of the injection setup protocol 140 was 10 ml/sec and the concentration from step 172 of the flow rate determination protocol 170 was 60%, the injector system 450 may calculate the target flow rate for the A side by multiplying the total target flow rate (10 ml/sec) by 0.6 to yield a target flow rate for the A side of 6 ml/sec, and the injector system 450 may calculate the target flow rate for the B side by multiplying the total target flow rate to (10 ml/sec) by 0.4 to yield a target flow rate for the B side of 4 ml/sec. Depending upon the magnitude of the concentration, the target flow rates for the A and B sides that are calculated by the medical fluid injector system 450 may not be exactly pro rata with the concentration (e.g., one or more factors may be implemented the further the concentration deviates from 50% of the first fluid 466a and 50% of the second fluid 466b).

The medical fluid injector system 450 also calculates the target pressure for both its A side and B side from both the target pressure (step 142 of the injection setup protocol 140; e.g., based in at least some manner upon user input, whether directly by a user entering a target pressure or indirectly by a user entering a peak pressure and from which a target pressure may be derived as noted above) and the concentration (step 172 of the flow rate determination protocol 170) pursuant to step 176 of the flow rate determination protocol 170. There are a number of options for having the injector system 450 calculate the target pressures for the A and B sides. In one embodiment, the target pressures for the A and B sides of the injector system 450 will simply be the corresponding percentage of the concentration (step 172), multiplied by the target pressure (step 142 of the injection setup protocol 140). For instance, if the target pressure from step 142 of the injection setup protocol 140 was 300 psi and the concentration from step 172 of the flow rate determination protocol 170 was 60%, the injector system 450 may calculate the target pressure for the A side by multiplying the target pressure (300 psi) by 0.6 to yield a target pressure for the A side of 180 psi, and the injector system 450 may calculate the target pressure for the B side by multiplying the target pressure (300 psi) by 0.4 to yield a target pressure for the B side of 120 psi. Depending upon the magnitude of the concentration, the target pressures for the A and B sides that are calculated by the medical fluid injector system 450 may not be exactly pro rata with the concentration (e.g., one or more factors may be implemented the further the concentration deviates from 50% of the first fluid 466a and 50% of the second fluid 466b).

In another embodiment, the target pressure for each of the A and B sides is initially set by the injector system 450 at the overall target pressure (step 142 of the injection setup protocol 140; e.g., based in at least some manner upon user input, whether directly by a user entering a target pressure or indirectly by a user entering a peak pressure and from which a target pressure may be derived as noted above). The individual target pressures for each of the A and B sides is then derived by the injector system 450 through subtracting a correction factor from this overall target pressure, and where the correction factor for each of the A and B sides is a result of a quadratic equation which uses the concentration (step 172 of the flow rate determination protocol 170) as an input.

It should be appreciated that the target flow rate and the target pressure for the A side and B side of the medical fluid injector system 450 could be calculated in any appropriate order and in accordance with the foregoing (e.g., step 176 could be executed before step 174). Once both the target flow rate and the target pressure for each of the A side and B side have been calculated by the medical fluid injector system 450, the flow rate determination protocol 170 returns control to the injection setup protocol 140 of FIG. 4 through execution of step 178.

Figure 6:
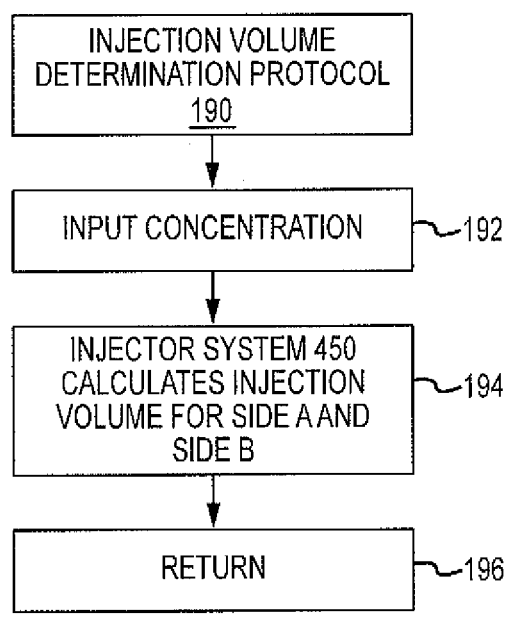
FIG. 6 is a schematic of an embodiment of an injection volume determination protocol that may be used by a medical fluid injector system.

One embodiment of an injection volume determination protocol that may be used by the injection volume determination module/logic 132 (FIG. 3C) is illustrated in FIG. 6 and is identified by reference numeral 190. As previously noted, the injection volume determination protocol 190 may be executed pursuant to step 158 of the injection setup protocol 140 (FIG. 4). In any case, the injection volume determination protocol 190 may be executed for the case where a phase of an injection protocol being programmed involves a simultaneous injection of multiple fluids (e.g., a simultaneous injection phase). Step 150 of the injection setup protocol 140 again is directed to inputting a total injection volume. The total injection volume that is entered pursuant to step 150 should be the total volume that is desired to be injected into the patient in a simultaneous injection configuration (e.g., where both the A side and B side of an medical fluid injector system 450 are simultaneously operated to simultaneously inject the first fluid 466a and the second fluid 466b into a patient). Data from step 150 of the injection setup protocol 140 may be used by the injection volume determination protocol 190 of FIG. 6, or the injection volume determination protocol 190 could be configured to independently acquire data on the total injection volume.

The concentration for the simultaneous injection phase being defined may be input to the medical fluid injector system 450 pursuant to step 192 of the injection volume determination protocol 190. Step 192 may be executed any time after an "AB" designation was selected pursuant to step 146 of the injection setup protocol 140. The discussion presented above with regard to the concentration and step 172 of the flow rate determination protocol 170 is also equally applicable to the concentration input step 192 of the injection volume determination protocol 190. Moreover and as previously noted, a user may only be required to input a concentration a single time for purposes of defining a simultaneous injection phase (i.e., the same concentration input may be used by each of the flow rate determination protocol 170 and the injection volume determination protocol 190).

The medical fluid injector system 450 calculates an injection volume for both its A side and B side from both the total injection volume (step 150 of the injection setup protocol 140) and the concentration (step 192 of the injection volume determination protocol 190) pursuant to step 194 of the injection volume determination protocol 190. In certain instances, the injection volumes for the A and B sides of the injector system 450 will simply be the corresponding percentage of the concentration, multiplied by the total injection volume. For instance, if the total injection volume (step 150 of protocol 140) was 100 ml and the concentration (step 192 of protocol 190) was 60%, the injector system 450 may calculate the injection volume for the A side by multiplying the total injection volume (100 ml) by 0.6 to yield an injection volume for the A side of 60 ml, and the injector system 450 may calculate the injection volume for the B side by multiplying the total injection volume (100 ml) by 0.4 to yield an injection volume for the B side of 40 ml. Depending upon the magnitude of the concentration, the injection volumes for the A and B sides that are calculated by the medical fluid injector system 450 may not be exactly pro rata with the concentration (e.g., one or more factors may be implemented the further the concentration deviates from 50% of the first fluid 466a and 50% of the second fluid 466b). In any case, once the injection volume for the A side and B side have been calculated by the medical fluid injector system 450, the injection volume determination protocol 190 returns control to the injection setup protocol 140 of FIG. 4 through execution of step 196.

Figure 7:
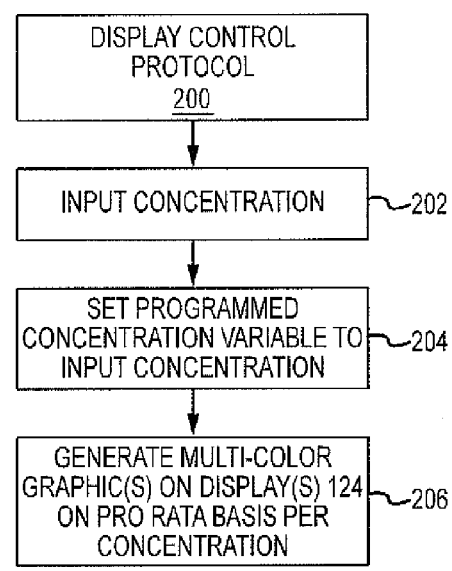
FIG. 7 is a schematic of an embodiment of a display control protocol that may be used by a medical fluid injector system.

One embodiment of a display control protocol that may be used by the display control module/logic 134 (FIG. 3C) is illustrated in FIG. 7 and is identified by reference numeral 200. Generally, the display control protocol 200 is directed to conveying concentration information on a simultaneous injection phase of an injection protocol using at least one multi-color graphic, where the relative amounts of multiple colors in such a multi-color graphic are correlated with the concentration.

Step 202 of the display control protocol 200 is directed to inputting a concentration value to the medical fluid injector system 450. Step 202 may be executed any time after an "AB" designation was selected pursuant to step 146 of the injection setup protocol 140. The discussion presented above with regard to the concentration and step 172 of the flow rate determination protocol 170 is also equally applicable to the concentration input step 202 of the display control protocol 200. The concentration for step 202 of the protocol 200 may be retrieved by the medical fluid injector system 450 from a simultaneous injection phase of a previously-defined injection protocol. The concentration for step 202 may also be input to the medical fluid injector system 450 in relation to a simultaneous injection phase that is currently being programmed into the medical fluid injector system 450. In any case, the value that is input pursuant to step 202 may be utilized for a programmed concentration variable (step 204). At least one multi-color graphic may be generated and presented on one or more displays 124 of the medical fluid injector system 450 (step 206) in accordance with the concentration from step 202. In one embodiment, the amount of the first fluid 466a to be injected in a given simultaneous injection phase corresponds with a first amount of a first color in one or more of such multi-color graphics, while the amount of the second fluid 466b to be injected in the same simultaneous injection phase corresponds with a second amount of a second color in one or more of such multi-color graphics.

The display control protocol 200 may be executed at any appropriate time. The display control protocol 200 may be executed as an injection protocol is being programmed, as an injection protocol is being edited, or as an injection protocol is being executed by the medical fluid injector system 450.

Figure 8:
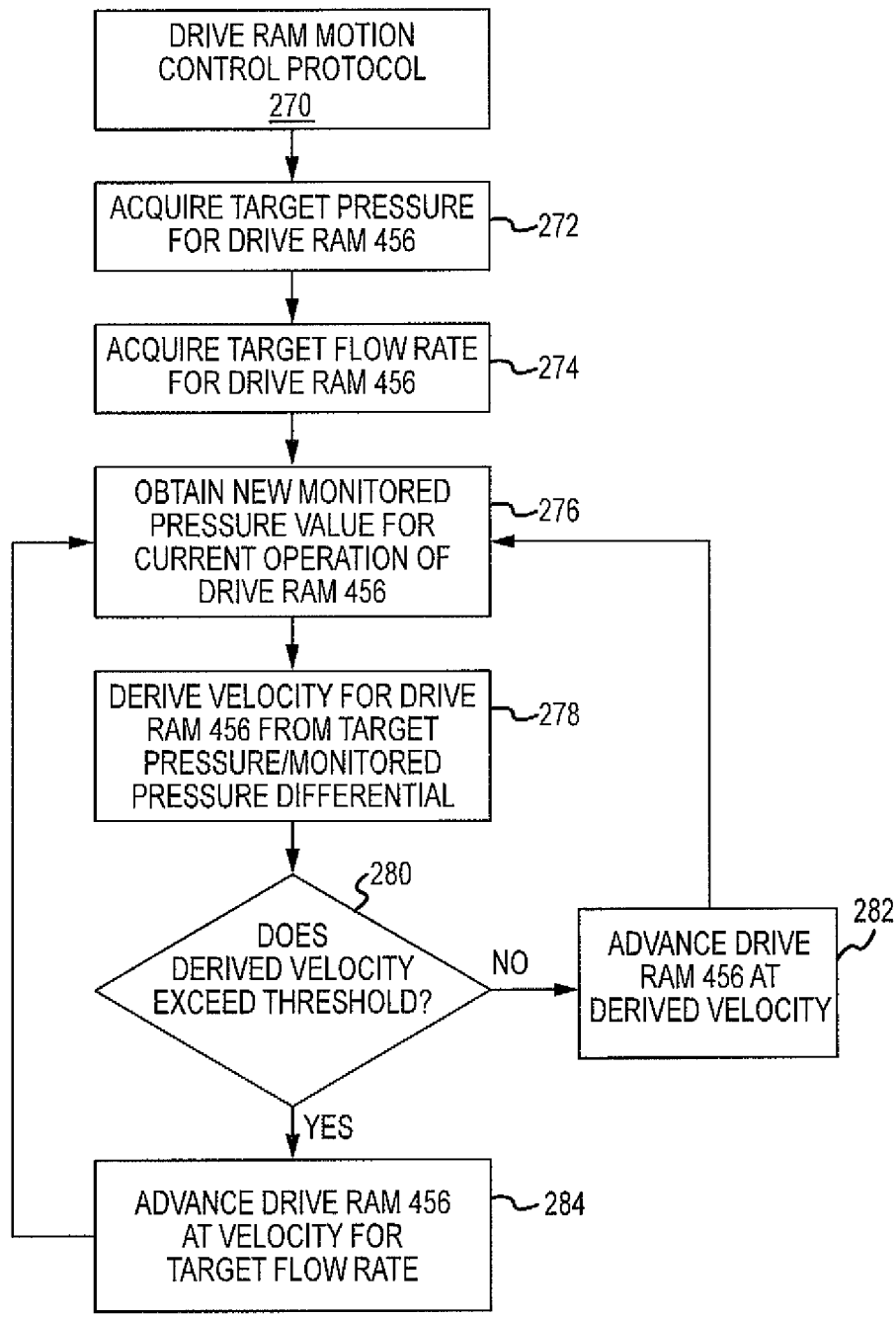
FIG. 8 is a schematic of an embodiment of a drive ram motion control protocol that may be used by a medical fluid injector system.

One embodiment of a drive ram motion control protocol that may be used by the drive ram motion control module/logic 136 (FIG. 3C) is illustrated in FIG. 8 and is identified by reference numeral 270. Generally, the drive ram motion control protocol 270 may be characterized as providing a pressure-based control of the velocity of a drive ram 456 (e.g., drive ram 456*a*; drive ram 456*b*) of a medical fluid injector system (e.g., medical fluid injector system 450). The drive ram motion control protocol 270 may be used to control the velocity of each drive ram 456*a*, 456*b* of the medical fluid injector system 450 of FIGS. 3B and 3C, whether being independently or simultaneously operated.

Step 272 of the drive ram motion control protocol 270 is directed to acquiring a target pressure associated with a drive ram 456 (e.g., drive ram 456*a*; drive ram 456*b*). In a non-simultaneous injection phase of an injection protocol, this may be a value that is set in response to user input (e.g., via step 142 of the injection setup protocol 140 of FIG. 4, as discussed above). In a simultaneous injection phase of an injection protocol, the target pressure for step 272 of the drive ram motion control protocol 270 may be provided by step 176 of the flow rate determination protocol 170 of FIG. 5.

Step 274 of the drive ram motion control protocol 270 is directed to acquiring a target flow rate for the drive ram 456. In a non-simultaneous injection phase of an injection protocol, this may be a value that is input by a user (e.g., via step 148 of the injection setup protocol 140 of FIG. 4). In a simultaneous injection phase of an injection protocol, the target flow rate for step 274 of the drive ram motion control protocol 270 may be provided by step 174 of the flow rate determination protocol 170 of FIG. 5.

Step 276 of the drive ram motion control protocol 270 is directed to obtaining a new or updated monitored pressure value for the current operation of the drive ram 456. This pressure may be acquired in any appropriate manner, including by execution of the pressure monitoring protocol 290 that will be discussed below in relation FIG. 9. In any case, the velocity for the drive ram 456 is derived from both the target pressure (step 272) and the monitored pressure (step 276) for the drive ram 456 pursuant to step 278, and including based upon a differential between these values.

Step 278 may be executed for a monitored pressure that is based upon a single point in time. Another option would be for step 278 to use a moving average of monitored pressures provided by step 276 (e.g., the monitored pressure value used by step 278 may be the average of the most recent "x" monitored pressure values provided by step 276). In any case and in the event that a determination is made pursuant to step 280 that the derived velocity for the drive ram 456 (step 278) does not exceed a threshold (e.g., a velocity for the drive ram 456 that should provide the target flow rate for the drive ram 456—step 274), step 282 may be used to advance the drive ram 456 at the derived velocity from step 278. However, in the event that a determination is made pursuant to step 280 that the derived velocity for the drive ram 456 (step 278) does exceed a threshold (e.g., a velocity for the drive ram 456 that should provide the target flow rate for the drive ram 456—step 274), step 284 may be used to advance the drive ram 456 at a velocity that should provide the target flow rate (step 274). Thereafter, a new monitored pressure value may be acquired (276), and steps 278 and 280 are repeated and in accordance with the foregoing.

A differential between the target pressure (step 272) and the monitored pressure (step 276) may be used to derive a velocity for the drive ram 446 in step 278 of the drive ram motion control protocol 270. Step 278 may be characterized as being directed to deriving a velocity value for the drive ram 456 in a manner that attempts to reduce the magnitude of an error between the target pressure (step 272) and the monitored pressure (step 276). In one embodiment, step 278 uses at least a two-term controller for deriving a drive ram velocity value from both the target pressure and an updated monitored pressure value (e.g., using a proportional term and a derivative term). In one embodiment, step 278 uses a PID controller (proportional-integral-derivative controller) for deriving a drive ram velocity value from both the target pressure and an updated monitored pressure value, although all three terms of such a controller may not in fact be utilized.

The drive ram motion control protocol 270 may be used to control the velocity at which a given drive ram 456 is advanced throughout an entirety of an injection protocol, and including in relation to each phase of an injection protocol. The drive ram motion control protocol 270 may be executed from the beginning of at least one phase of an injection protocol, and thereafter may be executed throughout the remainder of the relevant phase. On the first execution of step 278 for a given phase of an injection protocol, the monitored pressure from step 276 may be zero (i.e., the first execution of step 278 may be undertaken prior to advancing the drive ram 456 in any manner). This should coincide with a maximum error between the target pressure (step 272) and the monitored pressure (step 276). However, the drive ram motion control protocol 270 could be initiated with the drive ram 456 being advanced at some initial non-zero velocity for purposes of the first execution of step 278.

Figure 9:
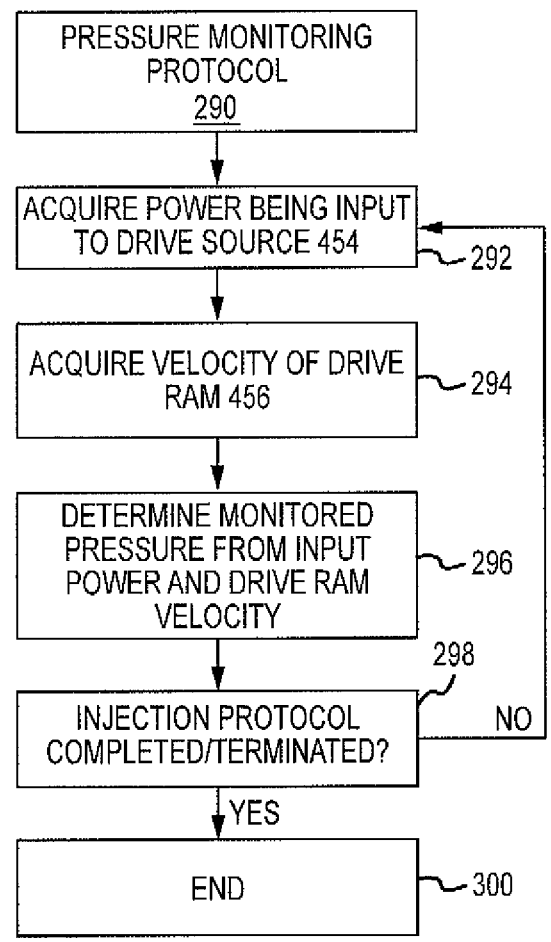
FIG. 9 is a schematic of an embodiment of a pressure monitoring protocol that may be used by a medical fluid injector system.

One embodiment of a pressure monitoring protocol that may be used by the pressure monitoring module/logic 138 (FIG. 3C) is illustrated in FIG. 9 and is identified by reference numeral 290. Generally, the pressure monitoring protocol 290 may be used to acquire a pressure associated with operation of a drive ram 456 (e.g., drive ram 456*a*, 456*b* of the medical fluid injector system 450) that is being advanced by a corresponding drive source 454 (e.g., drive source 454*a*, 454*b* of the medical fluid injector system 450). The power being input to the associated drive source 454 may be acquired in any appropriate manner (step 292). In one embodiment, the input power is acquired from a signal (e.g., from a controlling chip) that is currently being used to operate the drive source 454. The velocity of the drive ram 456 may be acquired in any appropriate manner (step 294). For instance, each drive source 454*a*, 454*b* may have an encoder wheel, which may be used to determine a velocity in revolutions per unit of time, and this may be converted into a linear velocity for the corresponding drive ram 456*a*, 456*b*.

A monitored pressure value may be determined (e.g., calculated or derived) from the input power (step 292) and the drive ram velocity (step 294) pursuant to step 296 of the pressure monitoring protocol 290 in any appropriate manner. In the event that the injection protocol has not yet been completed or terminated, the pressure monitoring protocol 290 may return to step 292 for repetition in accordance with foregoing. Otherwise the pressure monitoring protocol 290 may be terminated pursuant to step 300.

With further regard to step 296 of the pressure monitoring protocol 290 of FIG. 9, a family of curves (or a family of equations (e.g., an equation that defines a curve)) may be empirically derived that relate input power to pressure for each of a plurality of linear velocities (a curve or equation for each linear velocity). That is, for a given linear velocity, there may be a predefined input power versus pressure relationship. Therefore, knowing the velocity identifies the relevant curve/equation, and knowing the input power then allows the pressure to be determined therefrom. It should be appreciated that interpolation may be utilized (e.g., if there is not a predefined input power vs. pressure relationship for a given linear velocity).

FIGS. 10-13 illustrate representative screens or display outputs that may be utilized by the medical fluid injector system 450 shown in FIGS. 3B and 3C, including without limitation in relation to the execution of one or more of the protocols 140 (FIG. 4), 170 (FIG. 5), 190 (FIG. 6), and 200 (FIG. 7). Generally, each of these screens includes a plurality of graphics or graphical representations (e.g., icons or buttons). Each such graphic may be used in the programming of an injection protocol, to convey information regarding an injection protocol, or both.

Figure 10:
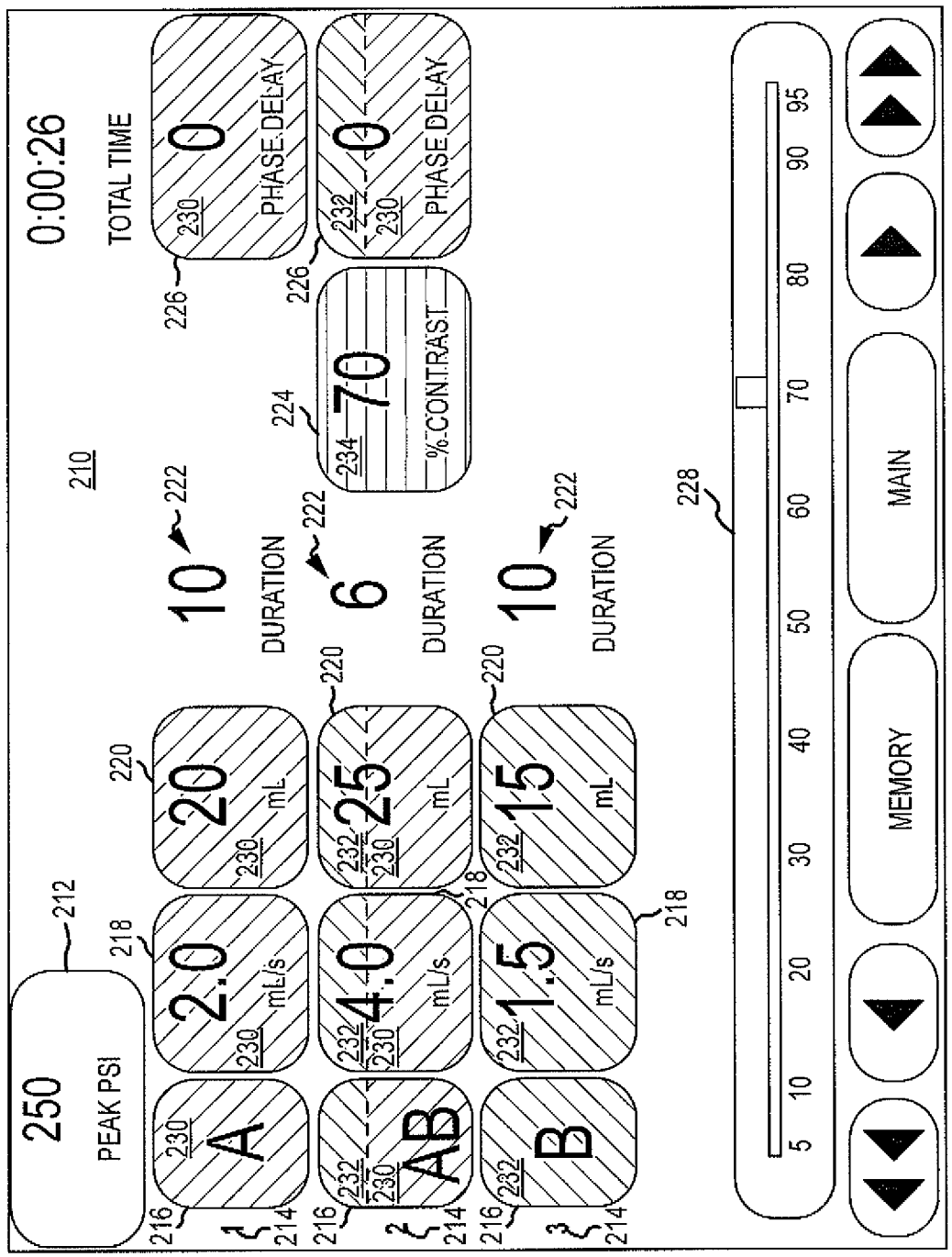
FIG. 10 is an embodiment of a screen from a medical fluid injector system during the programming of an injection protocol.

The screen or display output 210 shown in FIG. 10 may be presented on one or more displays 124 used by the medical fluid injector system 450. The screen 210 illustrates a representative programming of an injection protocol for the medical fluid injector system 450. Initially, the screen 210 presents a peak pressure icon/button 212. A single peak pressure may be programmed for an injection protocol, and may be used to control the velocity of the drive ram 456a and/or 456b of the medical fluid injector system 450 during a particular phase of an injection protocol in accordance with the drive ram motion control protocol 270 discussed above in relation to FIG. 8.

The injection protocol being programmed on the screen 210 shown in FIG. 10 includes three phases. Any appropriate number of phases may be programmed for an injection protocol and/or may be simultaneously presented on the screen 210. The screen 210 includes three phase icons or buttons 214—one for each phase of the injection protocol being programmed (the phase icon 214 in the form of a "1" coinciding with phase 1; the phase icon 214 in the form of a "2" coinciding with phase 2; and the phase icon 214 in the form of a "3" coinciding with phase 3). Each phase of the illustrated injection protocol being programmed and associated with the screen 210 (e.g., each phase icon 214) includes an associated drive ram icon/button 216, a total flow rate icon/button 218, a total injection volume icon/button 220, and a phase duration icon/button 222. All phases, other than the last phase of an injection protocol, may also include a phase delay icon/button 226. Therefore and in the case of the screen 210 shown in FIG. 10, a phase delay icon/button 226 is shown for each of phases 1 and 2 of the injection protocol being programmed, but not for phase 3.

The medical fluid injector system 450 may be programmed using the screen 210 shown in FIG. 10. A user may use the drive ram icon 216 to select which drive ram 456a, 456b of the medical fluid injector system 450 is to be advanced for the associated phase. Each drive ram icon 216 may be "toggled" (e.g., by a sequential touching or engagement of a particular drive ram icon 216) between at least three states or conditions—one condition being where only the A side of the medical fluid injector system 450 is operated (e.g., syringe plunger driver 452a) such that only the first fluid 466a is discharged into the tubing set 470; another condition being where only the B side of the medical fluid injector system 450 is operated (e.g., syringe plunger driver 452b) such that only the second fluid 466b is discharged into the tubing set 470; and another condition being where the A side and B side of the medical fluid injector system 450 are simultaneously operated (e.g., syringe plunger drivers 452a, 452b) such that both the first fluid 466a and second fluid 466b are simultaneously discharged into the tubing set 470. In the case of the injection being programmed on the screen 210 shown in FIG. 10: phase 1 entails operating only the A side of the medical fluid injector system 450 (e.g., via its corresponding drive ram icon 216 having been set to "A"); phase 2 entails simultaneously operating the A and B sides of the medical fluid injector system 450 (e.g., via its corresponding drive ram icon 216 having been set to "AB"); and phase 3 entails operating only the B side of the medical fluid injector system 450 (e.g., via its corresponding drive ram icon 216 having been set to "B").

Values for the total flow rate, total injection volume, phase duration, and phase delay of each phase may be entered by touching, engaging, or selecting (e.g., activating) the relevant total flow rate icon 218, total injection volume icon 220, phase duration icon 222, and phase delay icon 226. Activating any of the icons 218, 220, 222, and 226 may allow a user to enter the desired values using one or more data input devices 126 (FIG. 3C). The target pressure for the injection protocol being programmed may be set by activating the peak pressure icon 212 and entering the desired value using one or more data input devices 126 (FIG. 3C).

When a drive ram icon 216 of a given phase is set to an "AB" configuration (a configuration where the A and B sides of the medical fluid injector system 450 are simultaneously operated), a concentration icon/button 224 is generated on the screen 210 for the corresponding phase to allow a user to input the desired concentration. In the case of the screen 210 shown in FIG. 10, the drive ram icon 216 for the second phase has been disposed in an "AB" configuration, and as such a concentration icon 224 has been presented on the screen 210 to allow a user to enter the desired concentration. Moreover, a data input device 126 in the form of a slide bar 228 has also been presented on the screen 210. A user may use the slide bar 228 to input the desired concentration (e.g., 70% in the illustrated embodiment). Activating any total flow rate icon 218, total injection volume icon 220, phase duration icon 222, and phase delay icon 226 could produce a similar data input device 126 on the screen 210 for inputting associated values for the corresponding phase. The values presented by any such slide bar could of course be tailored to the parameter corresponding to the activated icon 218, 220, 222, and 226 (e.g., a slide bar presented on the screen 210 for entering a total flow rate for a phase may present an appropriate range of flow rate values, for instance from 0 ml/sec to 10 ml/sec; a slide bar presented on the screen 210 for entering a total injection volume for a phase may present an appropriate range of injection volume values, for instance up to 400 ml). The medical fluid injector system 450 may be configured to display a data input device 126 on a screen only for a certain amount of time after a given icon 212, 218, 220, 222, 224, 226 has been activated.

Information on various parameters of each phase of an injection protocol may be both graphically conveyed and numerically conveyed in the case of the medical fluid injector system 450. In this regard and continuing to refer to FIG. 10, some of the graphics may be presented in only a first color 230 (e.g., yellow), some of the graphics may be presented in only a second color 232 (e.g., purple or lavender), and some of the graphics may be presented in both a first color 230 and a second color 232.

Graphics on the screen 210 that are presented in only the first color 230 means that only a first fluid 466a is being delivered in the corresponding phase. Since the drive ram icon 216 has been set to the A side for phase 1 in the embodiment shown in FIG. 10, the entirety of each of the drive ram icon 216, the total flow rate icon 218, the total injection volume icon 220, and the phase delay icon 226 for the first phase shown on the screen 210 in FIG. 10 are presented only in the first color 230.

Graphics on the screen 210 that are presented in only the second color 232 means that only a second fluid 466b is being delivered in the corresponding phase. Since the drive ram icon 216 has been set to the B side for phase 3 in the embodiment shown in FIG. 10, the entirety of each of the drive ram icon 216, the total flow rate icon 218, and the total injection volume icon 220 for the third phase shown on the screen 210 in FIG. 10 are presented only in the second color 232.

Graphics on the screen 210 that are presented in both the first color 230 and second color 232 means that both first fluid 466a and second fluid 466b are being delivered (e.g., simultaneously injected) in the corresponding phase. Since the drive ram icon 216 has been set to the AB side for phase 2 in the embodiment shown in FIG. 10: one part of each of the drive ram icon 216, the total flow rate icon 218, the total injection volume icon 220, and the phase delay icon 226 for the second phase shown on the screen 210 in FIG. 10 are presented only in the first color 230; and the remainder of each of the drive ram icon 216, the total flow rate icon 218, the total injection volume icon 220, and the phase delay icon 226 for the second phase shown on the screen 210 in FIG. 10 is presented only in the second color 232. The amount of the first color 230 and the amount of the second color 232 included in each graphic corresponds (e.g., pro rata) with the concentration. In the embodiment illustrated in FIG. 10 where a concentration of 70% is being programmed for the second phase: 70% of each of the drive ram icon 216, the total flow rate icon 218, the total injection volume icon 220, and the phase delay icon 226 are presented in the first color 230; and 30% of each of the drive ram icon 216, the total flow rate icon 218, the total injection volume icon 220, and the phase delay icon 226 are presented in the second color 232.

The concentration icon 224 shown in FIG. 10 is actually presented in a third color 234 (e.g., beige). This may be used to convey to a user that the concentration of a particular phase is currently being programmed. Once programming of the concentration is complete for a particular phase, the concentration icon 224 may be presented in the same manner as other icons in the same phase. In this regard and now referring to FIG. 11, 70% of the concentration button 224 for the second phase of the injection protocol is presented in the first color 230, and 30% of the concentration button 224 for this second phase is presented in the second color 232. As programming of the injection protocol has been completed, the slide bar 228 from the screen 210 of FIG. 10 no longer appears on the screen 240 in FIG. 11.

Figure 11:
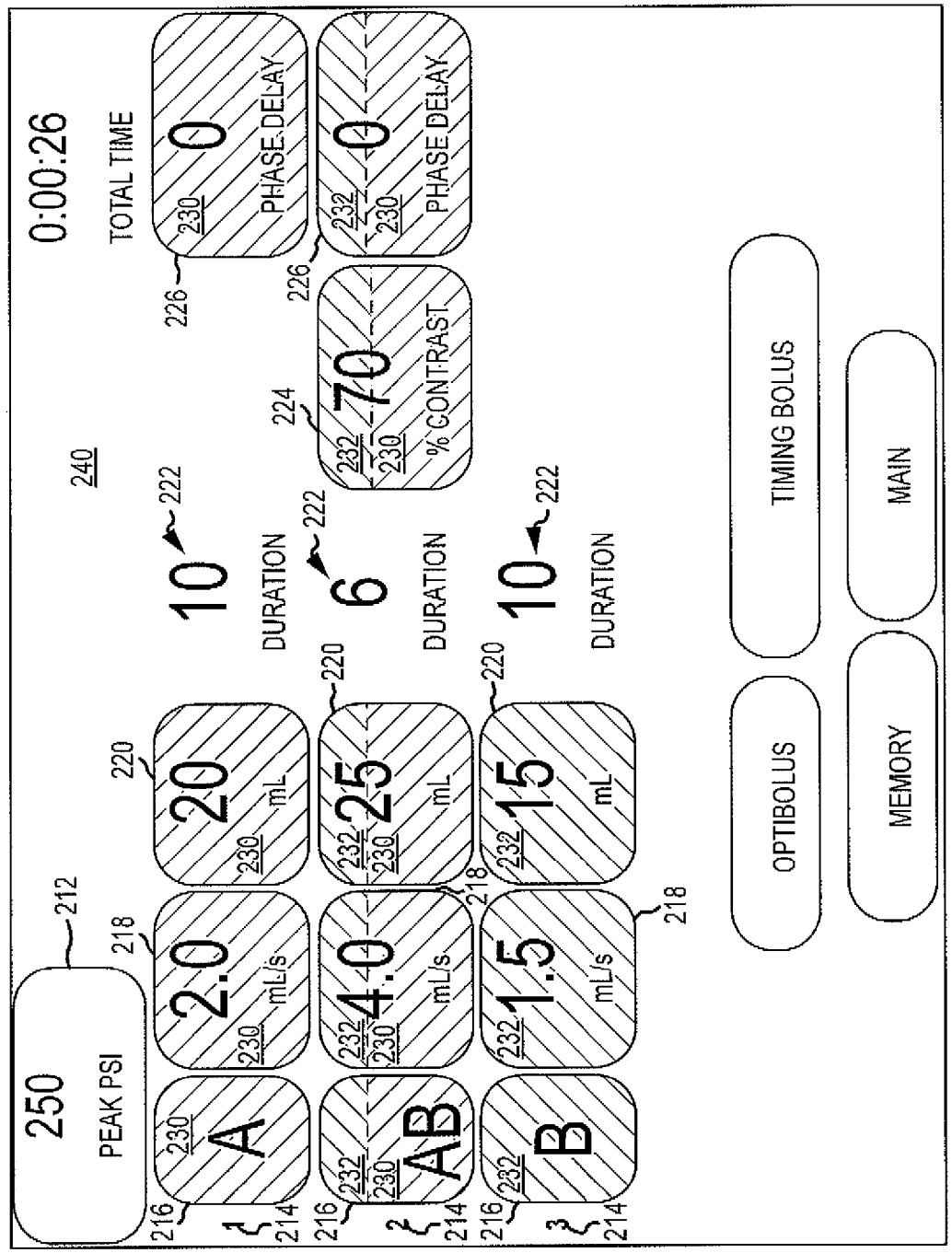
FIG. 11 is an embodiment of a screen from a medical fluid injector system after completing the programming of an injection protocol.

The concentration icon 224 shown in the screen 240 of FIG. 11 numerically conveys the programmed concentration (i.e., 70%), and furthermore graphically conveys the programmed concentration by correlating the amounts of the first color 230 and the second color 232 in the concentration icon 224 with the programmed concentration. Other of the icons presented on the screen 240 may convey information on two different parameters of a given phase. For instance, each of the drive ram icon 216, total flow rate icon 218, total injection volume icon 220, and phase delay icon 226 of each phase numerically convey a value of one parameter of the phase, and graphically conveys the programmed concentration by correlating the amounts of the first color 230 and the second color 232 in such icons 216, 218, 220, and 226 with the programmed concentration. As such: 1) each drive ram icon 216 numerically conveys the associated programmed drive ram (A, B, or AB), and also graphically conveys the programmed concentration by correlating the amounts of the first color 230 and the second color 232 in the respective drive ram icon 216 with the programmed concentration; 2) each total flow rate icon 218 numerically conveys the associated programmed flow rate, and also graphically conveys the programmed concentration by correlating the amounts of the first color 230 and the second color 232 in the respective total flow rate icon 218 with the programmed concentration; 3) each total injection volume icon 220 numerically conveys the associated programmed injection volume, and also graphically conveys the programmed concentration by correlating the amounts of the first color 230 and the second color 232 in the respective total injection volume icon 220 with the programmed concentration; and 4) each phase delay icon 226 numerically conveys the associated programmed phase delay, and also graphically conveys the programmed concentration by correlating the amounts of the first color 230 and the second color 232 in the respective phase delay icon 226 with the programmed concentration.

The screens 210, 240 from FIGS. 10 and 11 respectively may be presented on any appropriate display 124 of the medical fluid injector system 450 (FIGS. 3B and 3C), including a display incorporated by a powerhead of power injector (e.g., on display 434 of power injector 432 (FIG. 3A)), on a remote console operatively interconnected with a power injector and where the remote console and power injector are part of an injector system (e.g., remote console 404 (FIG. 3A)), on a common console that is operatively interconnected with both a medical imaging device and a power injector), or the like.

Figure 12:
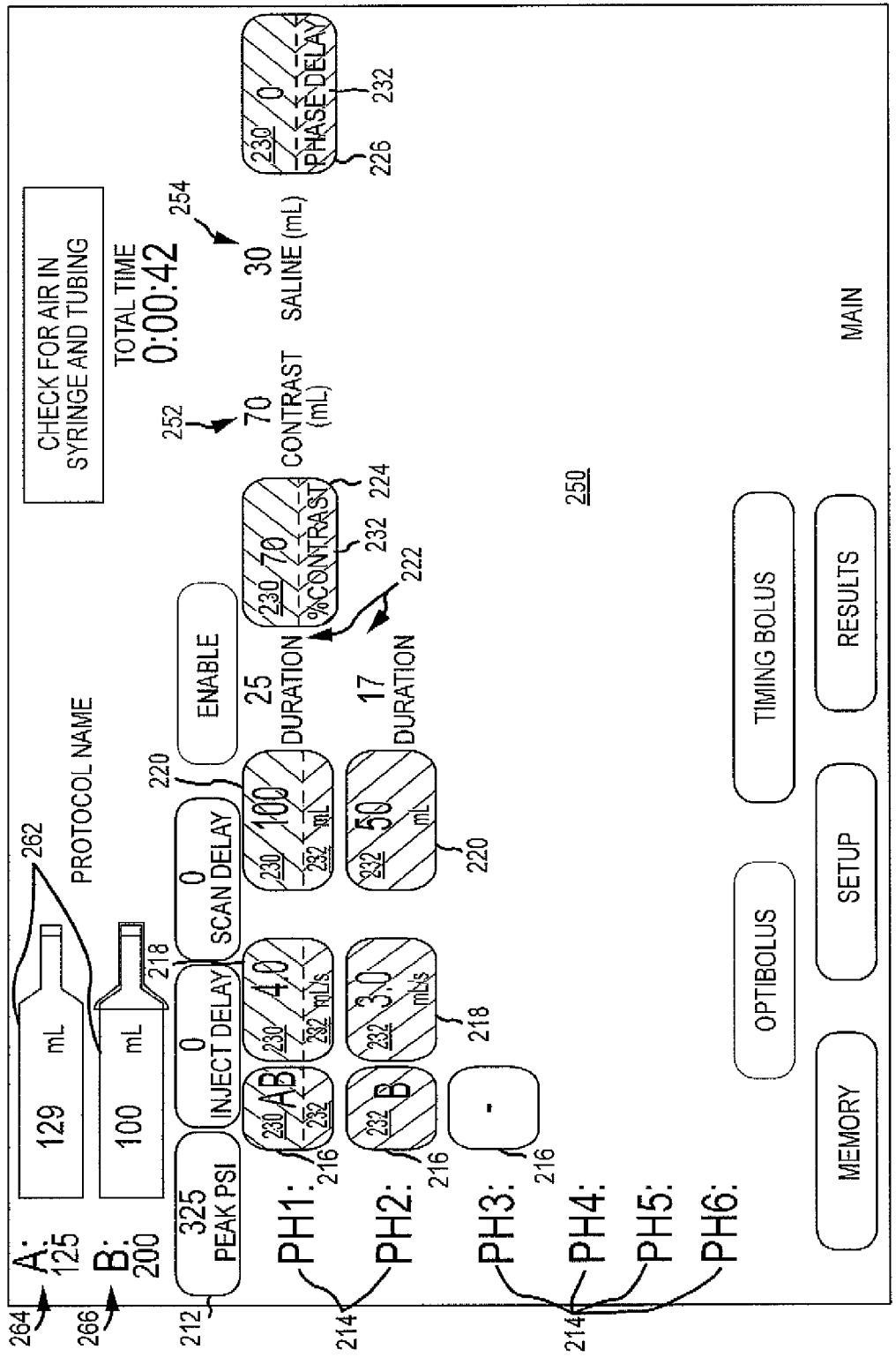
FIG. 12 is an embodiment of a screen from a medical fluid injector system after completing the programming of an injection protocol, and which utilizes multi-color graphics to convey a 70/30 concentration for one phase of the injection protocol.

FIG. 12 is a representative screen 250 that may be presented on any one or more displays 124 of the medical fluid injector system 450, including without limitation on a remote console of a contrast media/medical fluid injector system, on a common console for a medical imaging device/scanner and a power injector, or both. Corresponding graphics from the screen 210 of FIG. 10 and the screen 250 of FIG. 12 are identified by the same reference numerals. The injection protocol in the form shown on the screen 250 of FIG. 12 includes two phases. The phase icon 214 in the form of "PH1" coincides with phase 1 of the displayed injection protocol on the screen 250, the phase icon 214 in the form of a "PH2" coincides with phase 2 of the displayed injection protocol on the screen 250, and so forth.

There are a number of additional features shown on the screen 250 of FIG. 12. One is the drive ram icon 216 for phase 3. This particular drive ram icon 216 is blank or empty, except for a small dash, to convey that phase 3 has not yet been programmed. This type of drive ram icon 216 may be generated after the immediately preceding phase has been programmed, or once the programming of the immediately preceding phase has been initiated. A first activation of the drive ram icon 216 for phase 3 could toggle the same to an "A" configuration, a second activation of the drive ram icon 216 for phase 3 could toggle the same to a "B" configuration, and a third activation of the drive ram icon 216 for phase 3 could toggle to the same to an "AB" configuration.

Another feature incorporated by the screen 250 shown in FIG. 12 is the display of the volumes of the two fluids to be simultaneously injected in a simultaneous injection phase. In this regard, phase 1 of the injection protocol shown in FIG. 12 is a simultaneous injection phase that has been programmed to be a 70% concentration of a first fluid 466*a* and a 30% concentration of a second fluid 466*b*. Since the total injection volume was programmed as 100 ml for this simultaneous injection phase (phase 1) of this particular injection protocol (e.g., indicated on the total injection volume icon 220), the display control module/logic 134 may be configured to numerically display the volume of the first fluid 466*a* (via a total injection volume icon 252) and to numerically display the volume of the second fluid 466*b* (via a total injection volume icon 254) that are to be simultaneously injected. The values associated with the icons 252 and 256 on the screen 250 may be provided by the injection volume determination protocol 190 of FIG. 6.

Graphic representations 262 of two syringes are also shown on the screen 250—one corresponding with the A side of the medical fluid injector system 450, and the other corresponding with the B side of the medical fluid injector system 450. The A side designation icon 264 (a well as the volumetric capacity of the corresponding syringe—125 ml in the illustrated embodiment) may be presented in the first color 230 (as it is associated with the first fluid 466*a*). The B side designation icon 266 (a well as the volumetric capacity of the corresponding syringe—200 ml in the illustrated embodiment) may be presented in the second color 232 (as it is associated with the second fluid 466*b*).

Figure 13:
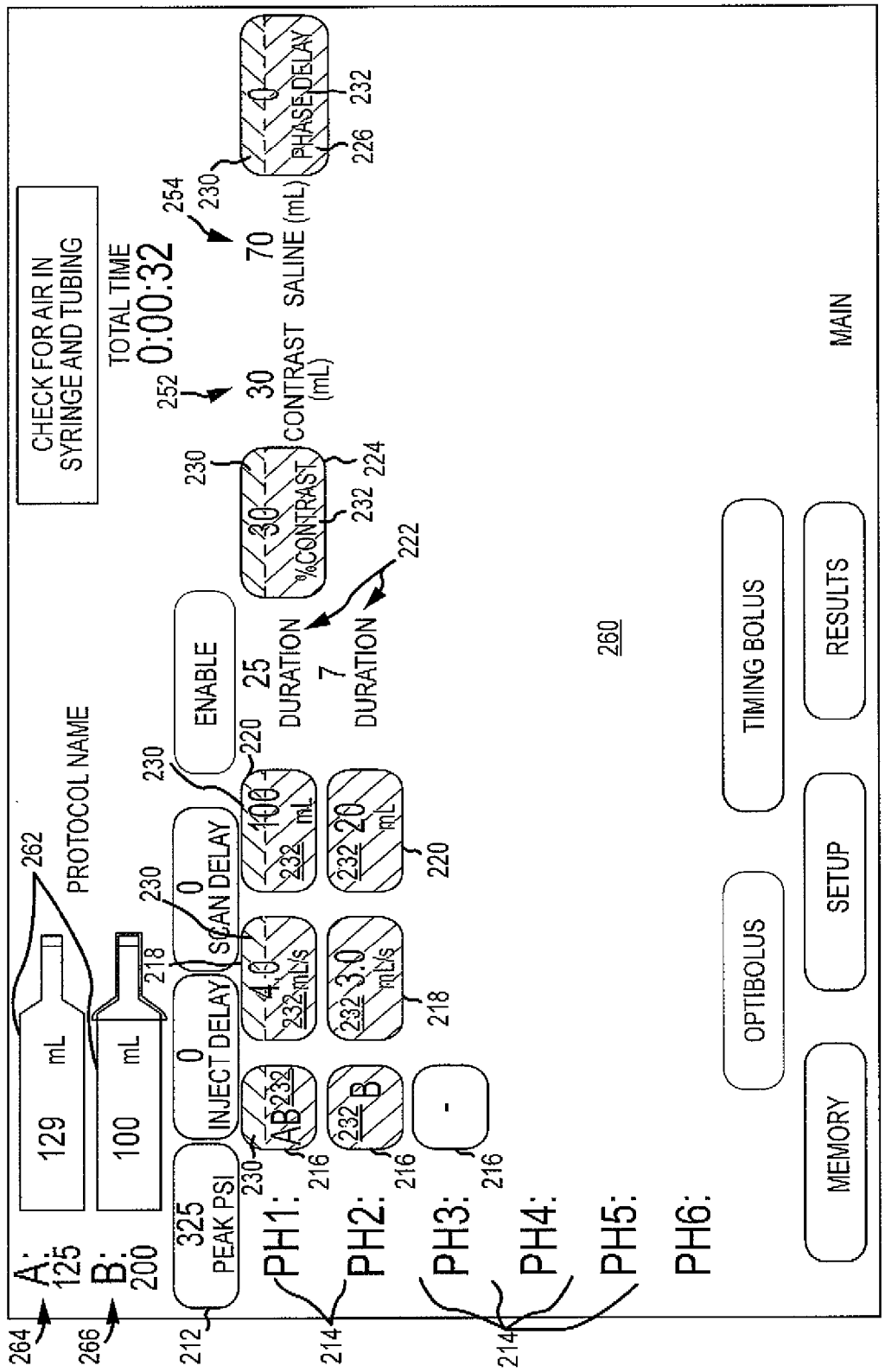
FIG. 13 is an embodiment of a screen from a medical fluid injector system after completing the programming of an injection protocol, and which utilizes multi-color graphics to convey a 30/70 concentration for one phase of the injection protocol.

FIG. 13 is another representative screen 260 that may be presented on any one or more displays 124 of the medical fluid injector system 450, including without limitation on a remote console of a contrast media/medical fluid injector system, on a common console for a medical imaging device/scanner and a power injector, or both. Corresponding graphics from the screen 250 of FIG. 12 and the screen 260 of FIG. 13 are identified by the same reference numerals, FIG. 13 illustrates a 30% concentration for phase 1 (a simultaneous injection phase). That is, phase 1 of the injection protocol shown in FIG. 13 is a simultaneous injection phase that has been programmed to be a 30% concentration of a first fluid 466*a* and a 70% concentration of a second fluid 466*b*. Since the total injection volume was programmed as 100 ml for this simultaneous injection phase (phase 1) of this particular injection protocol (e.g., indicated on the total injection volume icon 220), the display control module/logic 134 may be configured to numerically display the volume of the first fluid 466*a* (via a total injection volume icon 252—30 ml in the illustrated embodiment) and to numerically display the volume of the second fluid 466*b* (via a total injection volume icon 254—70 ml in the illustrated embodiment) that are to be simultaneously injected. The values associated with the icons 252 and 256 on the screen 260 may be provided by the injection volume determination protocol 190 of FIG. 6.

The power injector control module/logic 122, including any one or more of the injection protocol module/logic 128, the flow rate determination module/logic 130, the injection volume determination module/logic 132, the display control module/logic 134, the drive ram motion control module/logic 136, the pressure monitoring module/logic 138, along with any one or more of the protocols shown in FIGS. 4-9, may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. The power injector control module/logic 122, including any one or more of the injection protocol module/logic 128, the flow rate determination module/logic 130, the injection volume determination module/logic 132, the display control module/logic 134, the drive ram motion control module/logic 136, the pressure monitoring module/logic 138, along with any one or more of the protocols shown in FIGS. 4-9, may be implemented at any single location or at multiple locations that are interconnected in any appropriate manner (e.g., via any type of network).

Both an inject delay graphic and a scan delay graphic are presented on the screen 250 in FIG. 12 and on the screen 260 of FIG. 13. An "inject delay" may be characterized as a delay (typically in seconds) from the time an operator initiates an injection, until the injection as described by the programmed injection protocol actually begins, A "scan delay" may be characterized as a delay (typically in seconds) from the time the operator initiates an injection until image acquisition operations are initiated with the imaging device. In any case, activating either of the inject delay graphic and the scan delay graphic allows the respective delays to be programmed for an injection protocol. The current programmed values for the inject delay ("0" in the illustrated embodiment, and which may be a default) and for the scan delay ("0" in the illustrated embodiment, and which may be a default) may be displayed within the respective graphics. One or more setup screens may be presented on one or more displays 124 of the medical fluid injector system 450, and that may provide an option as to whether an inject delay graphic, a scan delay graphic, or both, should be presented on a screen when programming an injection protocol and/or when executing an injection protocol using the medical fluid injector system 450.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A medical fluid injector system comprising:
   a syringe plunger driver comprising a drive source and a drive ram, wherein said drive source is operable to advance said drive ram in a fluid discharge direction to cause a discharge of a medical fluid from a syringe when incorporated by said medical fluid injector system; and
   drive ram motion control logic configured to derive a drive ram velocity increase from a target pressure by deriving at least one drive ram velocity increase value, wherein said target pressure is associated with advancement of said drive ram in said fluid discharge direction, and wherein said target pressure is a single value throughout a first time range;
   wherein said drive ram motion control logic is configured to incrementally increase a drive ram velocity in view of said at least one drive ram velocity increase value during execution of a current phase of an injection protocol until an occurrence of a first condition, after which said drive ram motion control logic is configured to maintain said drive ram velocity at a value associated with satisfaction of said first condition for a continued execution of said current phase of said injection protocol;

wherein said first condition is satisfied by said medical fluid injector system reaching said target pressure during said current phase of said injection protocol without necessarily reaching a target flow rate for said current phase, and wherein said first condition is also satisfied by said medical fluid injector system reaching said target flow rate without necessarily reaching said target pressure.

2. The medical fluid injector system of claim 1, wherein said target flow rate comprises user input.

3. The medical fluid injector system of claim 1, wherein said drive ram motion control logic incrementally increases said drive ram velocity in view of said at least one drive ram velocity increase value throughout said first time range, wherein said first time range extends from a beginning of an associated phase of said injection protocol and until any occurrence of said first condition.

4. The medical fluid injector system of claim 1, wherein said target pressure comprises an independent variable, and wherein said at least one drive ram velocity increase value comprises a dependent variable.

5. The medical fluid injector system of claim 1, wherein said drive ram motion control logic is configured to repeatedly derive said at least one drive ram velocity increase value from said target pressure.

6. The medical fluid injector system of claim 5, wherein said drive ram motion control logic is configured to repeatedly derive said at least one drive ram velocity increase value from both said target pressure and a monitored pressure.

7. The medical fluid injector system of claim 6, wherein said drive ram motion control is configured to repeatedly derive said at least one drive ram velocity increase value from a differential between said target pressure and said monitored pressure.

8. The medical fluid injector system of claim 6, wherein said drive ram motion control logic is configured to repeatedly derive said at least one drive ram velocity increase value to reduce an error between said target pressure and said monitored pressure.

9. The medical fluid injector system of claim 6, wherein said drive ram motion control logic utilizes at least a two-term controller.

10. The medical fluid injector system of claim 9, wherein a proportional term and a derivative term are used by said controller.

11. The medical fluid injector system of claim 6, wherein said drive ram motion control logic utilizes a proportional-integral-derivative controller.

12. The medical fluid injector system of claim 1, wherein said drive ram motion control logic is configured to recursively derive said at least one drive ram velocity increase value from said target pressure.

13. The medical fluid injector system of claim 1, wherein said drive ram motion control logic is configured to iteratively derive said at least one drive ram velocity increase value from said target pressure.

14. The medical fluid injector system of claim 1, wherein said drive ram motion control logic is configured to derive said at least one drive ram velocity increase value both from said target pressure and a monitored pressure.

15. The medical fluid injector system of claim 14, wherein said drive ram motion control logic is configured to derive said drive ram velocity increase from a differential between said target pressure and said monitored pressure.

16. The medical fluid injector system of claim 14, wherein said drive ram motion control logic utilizes at least a two-term controller.

17. The medical fluid injector system of claim 16, wherein a proportional term and a derivative term are used by said controller.

18. The medical fluid injector system of claim 14, wherein said drive ram motion control logic utilizes a proportional-integral-derivative controller.

19. The medical fluid injector system of claim 1, wherein said target pressure is set in response to user input.

20. The medical fluid injector system of claim 1, wherein said target pressure comprises user input.

21. The medical fluid injector system of claim 1, wherein said first time range is an entirety of said current phase of said injection protocol.

22. The medical fluid injector system of claim 21, wherein said first time range is an entirety of said current phase and each of one or more additional phases of said injection protocol.

* * * * *